(12) United States Patent
Misselwitz et al.

(10) Patent No.: US 7,344,704 B2
(45) Date of Patent: Mar. 18, 2008

(54) USE OF PERFLUOROALKYL-CONTAINING METAL COMPLEXES AS CONTRAST MEDIA IN MR-IMAGING FOR VISUALIZATION OF INTRAVASCULAR THROMBI

(75) Inventors: Bernd Misselwitz, Glienicke (DE); Johannes Platzek, Berlin (DE); Yoko Kawata, Takarazuka (JP); Hanns-Joachim Weinmann, Berlin (DE); Takashi Yokawa, Tokyo (JP); Ulrich Niedballa, Berlin (DE)

(73) Assignee: Schering AG, Berlin (DE)

(*) Notice: Subject to any disclaimer, the term of this patent is extended or adjusted under 35 U.S.C. 154(b) by 610 days.

(21) Appl. No.: 10/616,511

(22) Filed: Jul. 10, 2003

(65) Prior Publication Data

US 2004/0131546 A1 Jul. 8, 2004

Related U.S. Application Data

(60) Provisional application No. 60/395,803, filed on Jul. 16, 2002.

(30) Foreign Application Priority Data

Jul. 10, 2002 (DE) ................. 102 31 799

(51) Int. Cl.
*A61B 5/055* (2006.01)
(52) U.S. Cl. ............... 424/9.363; 424/9.36; 424/9.321; 424/9.361; 424/9.362; 424/9.3; 424/9.1
(58) Field of Classification Search ............. 424/1.11, 424/1.65, 9.1, 9.3, 9.36, 9.361, 9.35, 9.363, 424/9.364, 9.365, 9.37, 9.362; 534/7, 10–16
See application file for complete search history.

(56) References Cited

U.S. PATENT DOCUMENTS

| 5,571,498 | A | 11/1996 | Cacheris et al. | |
|---|---|---|---|---|
| 6,019,959 | A * | 2/2000 | Platzek et al. | 424/9.36 |
| 6,461,587 | B1 * | 10/2002 | Platzek et al. | 424/9.323 |
| 6,468,502 | B1 | 10/2002 | Platzek et al. | |
| 6,565,828 | B2 | 5/2003 | Liu | |
| 6,641,797 | B2 * | 11/2003 | Platzek et al. | 424/1.65 |
| 6,676,928 | B2 | 1/2004 | Platzek et al. | |
| 6,743,412 | B2 | 6/2004 | Harris | |
| 6,818,203 | B2 * | 11/2004 | Platzek et al. | 424/9.363 |
| 2003/0072713 | A1 | 4/2003 | Platzek et al. | |

FOREIGN PATENT DOCUMENTS

| EP | 1088558 | | 4/2001 |
|---|---|---|---|
| WO | WO 9533494 | | 12/1995 |
| WO | WO 97/26017 | * | 7/1997 |
| WO | WO 9726017 | | 7/1997 |
| WO | WO 9816256 | | 4/1998 |
| WO | WO 99/01161 | * | 1/1999 |
| WO | WO 9901161 | | 1/1999 |
| WO | WO 0056723 | | 9/2000 |
| WO | WO 0108712 | | 2/2001 |
| WO | WO 0177102 | | 10/2001 |
| WO | WO 0213874 | | 2/2002 |
| WO | WO 0213875 | | 2/2002 |
| WO | WO 0214309 | | 2/2002 |

OTHER PUBLICATIONS

Yu Xin et al., "High-resolution MRI characterization of human thrombus using a novel fibrin-targeted paramagnetic nanoparticle contrast agent," Magnetic Resonance in Medicine, Dec. 2000, pp. 867-872, vol. 44, No. 6, XP001155744, ISSN: 0740-3194, the entire document.

* cited by examiner

*Primary Examiner*—Dameron L. Jones
(74) *Attorney, Agent, or Firm*—Millen, White, Zelano & Branigan, P.C.

(57) ABSTRACT

The invention relates to the use of perfluoroalkyl-containing metal complexes that have a critical micelle formation concentration $<10^{-3}$ mol/l, a hydrodynamic micelle diameter (2 Rh)>1 nm and a proton relaxivity in plasma ($R^1$)>10 l/mmol·s as contrast media in MR imaging for visualization of intravascular thrombi.

50 Claims, 3 Drawing Sheets

3D FLASH　　　　　　　　　Phase contrast

Image 1　　　　　　　　　Image 2

HE  PTAH

Image 3  Image 4

Abb. 5

Image 5

Abb. 6

Image 6

Abb. 7

Image 7

USE OF PERFLUOROALKYL-CONTAINING METAL COMPLEXES AS CONTRAST MEDIA IN MR-IMAGING FOR VISUALIZATION OF INTRAVASCULAR THROMBI

This application claims the benefit of the filing date of U.S. Provisional Application Ser. No. 60/395,803, filed Jul. 16, 2002.

The invention relates to the subject that is characterized in the claims, i.e., the use of perfluoroalkyl-containing metal complexes that have a critical micelle formation concentration $<10^{-3}$ mol/l, a hydrodynamic micelle diameter (2 Rh)>1 nm and a proton relaxivity in plasma $(R^1)>10$ l/mmol·s, as contrast media in MR-imaging for visualization of intravascular thrombi.

Thrombosis is defined as the formation of a blood clot (thrombus) in a blood vessel and the thus-induced constriction or clogging of this vessel. Most often, thromboses are found in the veins (phlebothrombosis). Here, preferably the veins of the lower half of the body (deep femoral and pelvic veins) are affected. Other portions of the circulatory system can also be affected, however: heart valves, apexei of the heart, coronary vessels, cerebral vessels, arteries in the area of the intestines, femoral arteries as well as veins of the leg and the pelvis, the rectum (hermorrhoids) and the arm. By moving the thrombus, a pulmonary embolism can result, which in the worst case ends in death.

Thromboses of the deep primary veins represent a significant social-medical problem. In Germany, 60,000 humans per year are treated for thromboses and their consecutive symptoms. In the USA, an acute thrombosis of the deep femoral veins of the leg and the pelvis occurs yearly in 48 out of a population of 100,000. About 12% of all stationary patients develop clinically detected deep femoral or pelvic vein thromboses. About 20 to 30% of all general-surgery patients and more than 50% of all patients after orthopedic/emergency surgical intervention suffer deep femoral vein thromboses, whereby in about 1% of these patients, a lung embolism with clinical symptoms occurs (Leitlinien zu Diagnostik und Therapie in der Gefäßchirurgie [Guidelines in Diagnosis and Therapy in Vascular Surgery], published by the Board of Directors of Dt. Ges. F. Gefäßchirurgie; Deutscher Ärzteverlag [German Society for Vascular Surgery; German Physicians' Publishing House], Cologne 1998).

The decisive mechanisms that cause a thrombosis were already described in 1856 by Rudolf Virchow and named by him as Virchow's Triad. In this case, this is damage to the vascular wall, slowing of the blood flow and an elevated blood-clotting tendency because of a change in the blood composition. While for the venous thrombosis (phlebothrombosis), the slowing of the blood flow and an elevated clotting tendency are emphasized, damage to the vascular wall, in most cases as a result of arteriosclerosis, with the deposit of blood platelets (thrombocytes) is of decisive importance in the development of the rare arterial thrombosis.

The thrombus maintains its original form only for a few days. After a structural transformation, it can be transformed as a scar in its final state, and the vessel is partially passable again (rechanneled). The purpose of this therapy is primarily the restoration of the blood flow. This therapy depends on the age of the thrombus and is successful only within the first 10 days after the thrombus develops. The restoration of the blood flow can be carried out, on the one hand, by a medicinal dissolution of the thrombus (thrombolysis). On the other hand, surgical methods are available: either the removal of the occlusion by removal of the clot (thrombectomy) or the bridging of the occluded vascular segment by an angioplasty (bypass). In the second place, the object of the therapy of the thrombosis is to prevent additional growth of the thrombus and to avoid late sequelae or complications.

The diagnosis of thromboses in clinical practice is mainly carried out by imaging processes. A very suitable method for detecting a thrombosis as well as for determining its extent is the radiological contrast medium study (phlebography). Drawbacks are the exposure to ionizing rays and the side-effects that are associated with iodine-containing contrast media. The initial examination method in the suspicion of low femoral vein thrombosis in many clinical devices is therefore the color-coded duplex sonography (B-scan plus PW Doppler), which is extremely dependent on the examiner, however. Other non-invasive imaging processes for visualizing luminal vascular changes are arteriography, CT angiography and MR angiography, as well as methods of nuclear medicine.

Thrombi thus can be visualized by blood corpuscles that are labeled with indium-111 as imaging agents (Thakur et al., Thromb. Res. 9: 345, 1976; Powers et al., Neurology 32: 938, 1982). The iodine isotopes J-125 and J-131 are also suitable for imaging purposes (Pang, U.S. Pat. No. 5,011,686, 1991). The technetium isotope Tc-99m is widely used as a label. Peptides and especially monoclonal antibodies are labeled with it (Berger, U.S. Pat. No. 5,024,829, 1991; Dean et al., U.S. Pat. No. 4,980,148, 1990: U.S. Pat. No. 5,508,020, 1996; U.S. Pat. No. 5,645,815, 1997; WO 00/61195; U.S. Pat. No. 6,171,578, 2001; EP 1171166, 2002). Compounds that are suitable both for scintigraphy and for MR imaging are described by Abelman (U.S. Pat. No. 5,656,600, 1997). In WO 01/77102, DuPont Pharmaceuticals describes conjugates from metal complexes and pyridinones, which are suitable as contrast media for diagnosis of thromboses with the aid of scintigraphy, computer tomography or MR imaging.

The literature for MR angiography for visualizing intravascular thrombi has a broad scope. Application WO 95/09013 describes cytogene polypeptides as complexing agents for paramagnetic metal ions.

In Application WO 95/24225, Nycomed named polymer complexing agents for thrombus imaging. Complexing agents such as DOTA or D03A are bonded to a backbone—for example, polylysine.

In WO 95/20603, Sandoz describes paramagnetic DTPA conjugates, which are suitable for the thrombus imaging.

In the Barne-Jewish Hospital Patent U.S. Pat. No. 5,780,010, specifically binding (biotin-avidin complexes) conjugates are described as contrast media for thrombus imaging. Also, in WO 98/16256, the Burnham Institute describes radicals that specifically bind (to integrin) and that make possible a thrombus imaging.

In these conjugates, paramagnetic complexes of DTPA, EDTA or DOTA are contained as signaling radicals.

Conjugates that consist of a guanidine derivative and paramagnetic complexes are described by 3-Dimensional Pharmaceuticals as contrast media for the thrombus imaging in WO 01/04117.

Conjugates that consist of complexes of DTPA, DOTA or D03A and polypeptides are described by EPIX in WO 01/09188 and EP 1203026 as imaging agents for the thrombus imaging.

In EP 885545, Pilgrimm names superparamagnetic iron oxides as contrast media for thrombosis diagnosis with the aid of MRI.

The MR contrast medium that is described in WO 02/22011 for the diagnosis of thrombi is also particulate (USPIO).

It is disadvantageous in the case of the conjugates that in addition to the diagnostically active portion, they contain another component (peptide or pharmaceutical agent), such that side effects, such as, for example, reduced compatibility, occur more often.

Of the particulate contrast media, the thrombus visualization of EP 885545 is described but not confirmed by experiment.

In WO 02/22011, images are shown, but the latter are obtained according to T2*-weighted flash sequences, such that the thrombi are only signal-free after the administration of contrast medium.

The examination of the blood of the patient for the presence of an elevated concentration of D-dimers has recently gained considerable clinical importance. According to associated studies, a concentration of less than 500 µg/l of D-dimers in the blood rules out the presence of a thromboembolism with very high probability (Wells, P. S. Brill-Edwards, P., Stevens, P. et al. A Novel and Rapid Whole Blood Assay for D-Dimer in Patients with Clinical Suspected Deep Vein Thrombosis. Circulation 1995; 91: 2184-2187). The specificity of the D-dimer detection is low, however, such that a thrombosis cannot be deduced from an increase of the concentration in the blood.

Obtaining images with the aid of nuclear magnetic resonance (MRI) is a modern, non-invasive radiological process, which makes possible the visualization of physiological and pathophysiological structures with a very good space and time resolution. In the diagnosis of deep femoral and pelvic vein thrombosis, the MR venography (MRV) has been methodically established for quite a long time as an alternative to phlebography and color-coded Doppler sonography (FKDS) in the area of the suprapopliteal veins. In recent years, studies on the MRV of the deep femoral veins were also published.

From the data record of a contrast-enhanced 3D-MR-angriography, the venous system basically can be selectively visualized by perfusion phase subtraction and directly visualized via an instep vein after injection of a dilute paramagnetic contrast medium. In the case of MR angiography with usual, extracellular, paramagnetic substances, a homogeneous vascular contrast is not always achieved, which impedes an evaluation in individual cases. With the expected use of highly concentrated contrast media or so-called "blood pool agents," however, the faster, contrast medium-supported 3D-MRA could be advantageous. With T2-turbo-spinecho (TSE) and Time-of-Flight (TOF)-sequences (without contrast medium), an adequate signal level can also be achieved in the open lower field tomograph (König, C. et al., MR-Venographie am offenen Niederfeldtomographen unter Verwendung manueller Flussaugmentation [MR Venography in the Open Lower-Field Tomograph with Use of Manual Flow Augmentation; Rofo, Fortschr. Geb. Röntgenstr. Neuen Bildgeb. Verfahr. 2001; 173: 810-814). Flow-sensitive MRA techniques, however, are less suitable for the diagnosis of thromboses, since in veins, especially in those with a thrombosis, the flow rate in the non-thrombosed portion is often too low.

The use of specific contrast media with selective concentration in certain tissues and organs could increase the diagnostic value of the MR imaging considerably. Contrast medium preparations with selective concentration in intravascular thrombi were able to detect location and degree of the disease at an early time and thus to make possible a targeted therapy and prophylaxis.

In addition, there is therefore a need for a compatible, powerful contrast medium for visualizing arterial and venous thromboses.

The object of this invention was therefore to make available contrast media for the visualization of intravascular thrombi in MR imaging that meet the requirements for Selective concentration
High compatibility
Strong enhancement
Complete elimination
And good water solubility.

It has now been found, surprisingly enough, that perfluoroalkyl-containing metal complexes, which have a critical micelle formation concentration $<10^{-3}$ mol/l, a hydrodynamic micelle diameter (2 Rh>1 nm) and a proton relaxivity in plasma ($R^1$)>10 l/mmol·s, are very well suited as contrast media in MR imaging for visualizing intravascular thrombi.

Compounds with these properties were already described in WO 02/13874 as diagnostic agents for plaque imaging with the aid of MR technology.

The MR images clearly show, however, that plaques and thrombi can be distinguished clearly from one another. This is therefore important, since thrombi in the young stage can be mobile and can result in lethal embolisms.

For the following tests, the gadolinium complexes were used, since the gadolinium of all paramagnetic ions has the greatest influence on the signal amplification in the MRI.

In an in-vitro test (binding to a fibrin gel), it was possible to prove that the compounds according to the invention bind to the fibrin gel at a concentration of 0.01 mmol of Gd/l to 79% and at a concentration of 0.1 mmol of Gd/l to 39% and thus make possible a reliable differentiation from plaque.

In addition, the contrast behavior of the compounds according to the invention was also examined in vivo. In rabbits with photochemically induced thrombus (PIT; i.v. injection of rose-Bengal and irradiation with xenon light), a considerable enhancement in the induced thrombus could be observed at various times after intravenous administration of 0.1 mmol of Gd/kg of body weight of the compound according to the invention (2 to 48 hours p.i.) with T1-weighted sequences. At the time of 24 hours p.i., the gadolinium concentration in the thrombus was about 4× higher compared to the blood.

For the MRI imaging, gadolinium concentrations of at least 50 µmol/l and at most 2500 µmol/l are required in the thrombus, where the concentration of the compound is carried out. The imaging can be done after 15 minutes or up to 48 hours after injection of the compounds according to the invention. Since primarily the T1-relaxation times of the tissue are influenced with the gadolinium complexes according to the invention, T1-weighted sequences are best able to detect an enhancement in the thrombus.

Amphiphilic compounds that as a nonpolar portion have a perfluoroalkyl side chain in the molecule that is optionally connected via a lipophilic linker with the total molecule are defined as perfluoroalkyl-containing metal complexes that are suitable for use according to the invention. The polar portion of the compounds according to the invention is formed by one or more metal complexes and optionally present additional polar groups.

In aqueous systems, these amphiphilic molecules show the properties that are characteristic of standard surfactants (such as, e.g., sodium dodecylsulfate, SDS). They thus reduce the surface tension of water. By tensiometry, the so-called CMC (critical micelle formation concentration in mol/l) can be determined. In this respect, the surface tension is determined based on the concentration of the substance to be measured. The CMC can be calculated from the plot of the surface tension function (c) that is obtained. The critical micelle formation concentration of the compounds according to the invention must be $<10^{-3}$ mol/l, preferably $<10^{-4}$ mol/l.

The amphiphilic compounds according to the invention are associated in solution and are present as aggregates. The size (2 Rh) of such aggregates (e.g., micelles, rods, wafers, etc.) can be determined with the aid of photon-correction spectroscopy (PCS).

As a second criterion, the hydrodynamic micelle diameter 2 Rh, which must be >1 nm, is therefore used. In particular, those perfluoroalkyl-containing metal complexes according to the invention whose 2 RH≧3 nm, quite especially preferably >4 nm, are suitable.

Both the determination of the CMC and the photon correlation spectroscopy are described in H.-D. Dörfler, "Grenzflächen-und Kolloidchemie [Interface and Colloid Chemistry]," Weinheim, New York, Basel, Cambridge, Tokyo, VSH 1994.

As a third criterion, the proton-relaxivity in plasma ($R^1$) at 40° C. and a field strength of 0.47 tesla are used. The relaxivity, which is indicated in [l/mmol·s], is the quantitative measurement for the shortening of relaxation time $T^1$ of the protons. For the purpose according to the invention, the relaxivity must be as high as possible and >10 l/mmol·s, preferably >13 l/mmol·s, especially preferably >15 l/mmol·s.

Relaxivity $R^1$ [l/mmol·s] of the MR-contrast media according to the invention was determined with the Minispec P 20 device of the Bruker Company. The measurements were taken at 40° C. and a field strength of 0.47 tesla. Eight measuring points were recorded by each T1-sequence: 180°-TI-90°, inversion recovery. As a medium, bovine plasma of the Kraeber Company was used. The contrast medium concentrations [mmol/l] in the batches were between 0.30 and 1.16.

In an embodiment of this invention, the compounds of general formula I according to aspects 8 to 11 are used as preferred compounds. In this case, these are known compounds that are described in WO 97/267017. Their production can also be found in this WO publication. Surprisingly enough, it has been shown that these compounds are also very well suited as MRI-contrast media for visualization of thrombi. As quite especially preferred compounds, metal complexes MK 2, 3 and 4, as well as MK 8, 9, 10 and 11 (cf. also Table 1) are used.

Aspect is 8 is the use according to the invention, wherein as perfluoroalkyl-containing metal complexes, the compounds of general formula I are used $$R^F\text{-L-K} \qquad \qquad I$$

in which
  $R^F$ is a perfluorinated, straight-chain or branched carbon chain with formula $—C_nF_{2n}E$, in which
    E represents a terminal fluorine, chlorine, bromine, iodine or hydrogen atom and n stands for numbers 4-30,
  L means a direct bond, a methylene group, an —NHCO group, a group

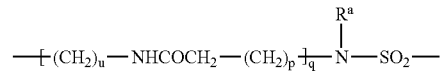

whereby p means the numbers 0 to 10, and q and u, independently of one another, mean numbers 0 or 1, and $R^a$ is a hydrogen atom, a methyl group, a benzyl group, a phenyl group, a —$CH_2$—OH group, a $CH_2OCH_3$ group, a —$CH_2$—$CO_2$H group or a $C_2$-$C_{15}$ chain, which optionally is interrupted by 1 to 3 oxygen atoms, 1 to 2 >CO groups or an optionally substituted aryl group and/or is substituted with 1 to 4 hydroxyl groups, 1 to 2 $C_1$-$C_4$ alkoxy groups, 1 to 2 carboxy groups, or a group —$SO_3$H—, or is a straight-chain, branched, saturated or unsaturated $C_2$-$C_{30}$ carbon chain, which optionally contains 1 to 10 oxygen atoms, 1 to 3 —$NR^a$ groups, 1 to 2 sulfur atoms, a piperazine, a —$CONR^a$ group, one to six —$NR^aCO$ groups, an —$SO_2$ group, an —$NR^a$—$CO_2$ group, 1 to 2 CO groups, a group

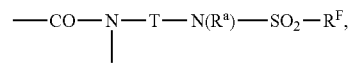

or 1 to 2 optionally substituted aryls and/or is interrupted by these groups and/or is optionally substituted with 1 to 3 —$OR^a$ groups, 1 to 2 oxo groups, 1 to 2 —NH—$COR^a$ groups, 1 to 2 —$CONHR^a$ groups, 1 to 2 —$(CH_2)_p$—$CO_2$H groups, 1 to 2 groups —$(CH_2)_p$—$(O)_q$—$CH_2CH_2$—$R^F$, whereby
  $R^a$, $R^F$ and p and q have the above-indicated meanings, and
  T means a $C_2$-$C_{10}$ chain, which optionally is interrupted by 1 to 2 oxygen atoms or 1 to 2 —NHCO groups,
K stands for a complexing agent or metal complex or their salts of organic and/or inorganic bases or amino acids or amino acid amides, specifically for a complexing agent or complex of general formula II

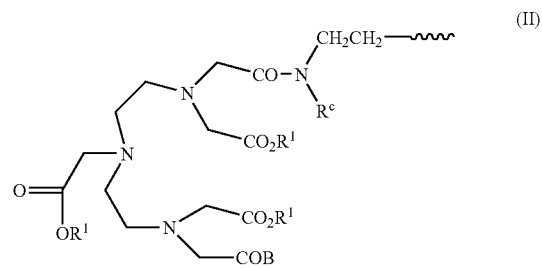

in which $R^c$, $R^1$ and B are independent of one another, and
  $R^c$ has the meaning of $R^a$ or means —$(CH_2)$m-L-$R^F$, whereby m is 0, 1 or 2, and L and $R^F$ have the above-mentioned meaning,
  $R^1$, independently of one another, mean a hydrogen atom or a metal ion equivalent of atomic numbers 22-29, 42-46 or 58-70, B means —OR¹ or

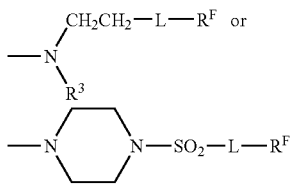

whereby R¹, L, R^F and R^c have the above-mentioned meanings, or

K stands for a complexing agent or complex of general formula III

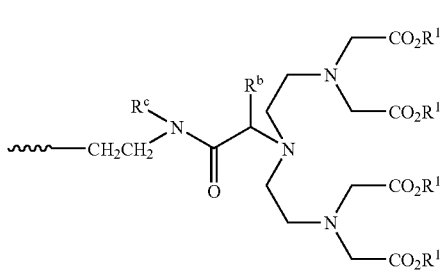
(III)

in which R^c and R¹ have the above-mentioned meanings,

R^b has the meaning of R^a, or

K stands for a complexing agent or complex of general formula IV

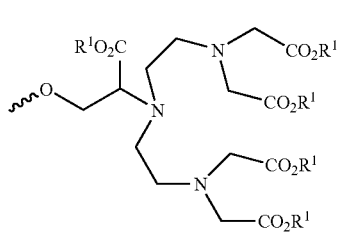
(IV)

in which R¹ has the above-mentioned meaning or

K stands for a complexing agent or complex of general formula V

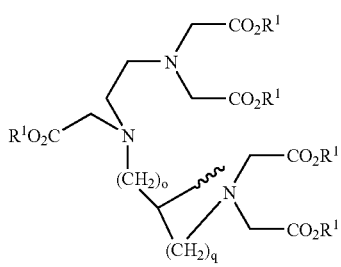
(V)

in which R¹ has the above-mentioned meaning, and o and q stand for number 0 or 1, and yields the sum o+q=1, or K stands for a complexing agent or complex of general formula VI

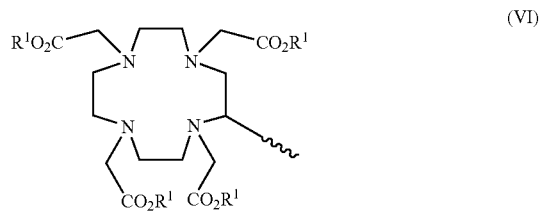
(VI)

in which R¹ has the above-mentioned meaning or

K stands for a complexing agent or complex of general formula VII

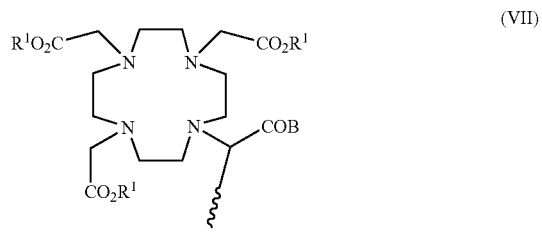
(VII)

in which R¹ and B have the above-mentioned meanings or

K stands for a complexing agent or complex of general formula VIII

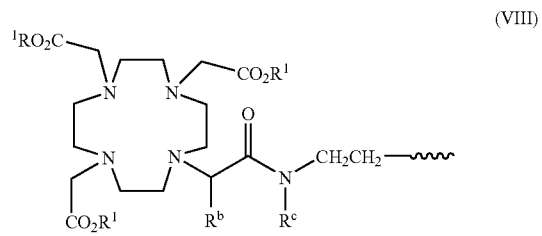
(VIII)

in which R^c and R¹ have the above-mentioned meanings, and R^b has the above-mentioned meaning of R^a or K stands for a complexing agent or complex of general formula IX

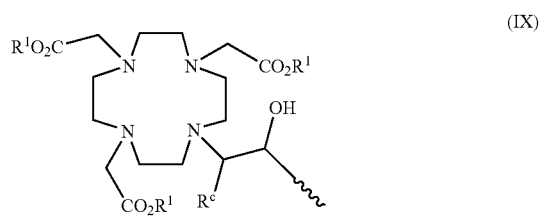
(IX)

in which $R^c$ and $R^1$ have the above-mentioned meanings, or

K stands for a complexing agent or complex of general formula X

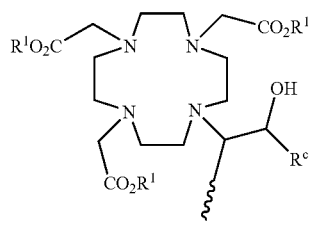

(X)

in which $R^c$ and $R^1$ have the above-mentioned meanings, or

K stands for a complexing agent or complex of general formula XI

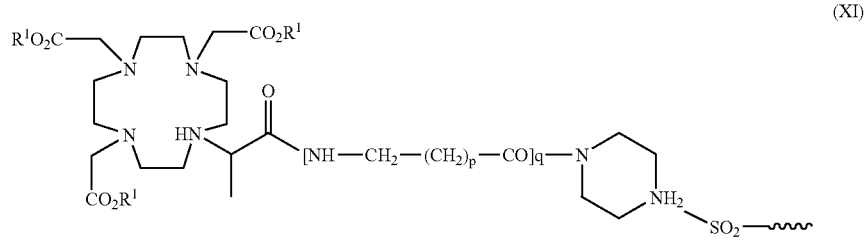

(XI)

in which $R^1$, p and q have the above-mentioned meaning, and $R^b$ has the meaning of $R^a$, or K stands for a complexing agent or complex of general formula XII

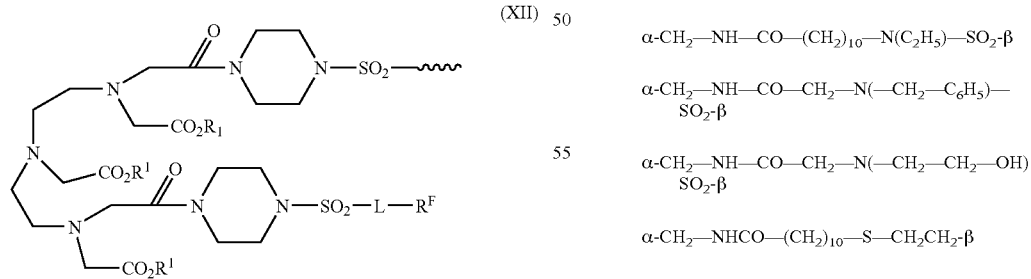

(XII)

in which L, $R^F$ and $Z^1$ have the above-mentioned meanings, or

K stands for a complexing agent or complex of general formula XIII

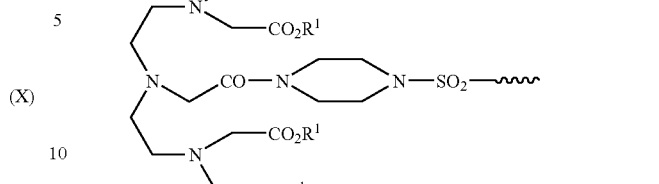

(XIII)

in which $R^1$ has the above-mentioned meaning, are used.

Aspect 9 is the use according to aspect 8, wherein the compounds of general formula I, in which L stands for

α-$CH_2$-β

α-$CH_2CH_2$-β

α-$(CH_2)_s$-β s=3-15

α-$CH_2$—O—$CH_2CH_2$-β

α-$CH_2$—(O—$CH_2$—$CH_2$—)$_t$-β t=2-6

α-$CH_2$—NH—CO-β

α-$CH_2$—NH—CO—$CH_2$—N($CH_2COOH$)—$SO_2$-β

α-$CH_2$—NH—CO—$CH_2$—N($C_2H_5$)—$SO_2$-β

α-$CH_2$—NH—CO—$CH_2$—N($C_{10}H_{21}$)—$SO_2$-β

α-$CH_2$—NH—CO—$CH_2$—N($C_6H_{13}$)—$SO_2$-β

α-$CH_2$—NH—CO—$(CH_2)_{10}$—N($C_2H_5$)—$SO_2$-β

α-$CH_2$—NH—CO—$CH_2$—N(—$CH_2$—$C_6H_5$)—$SO_2$-β

α-$CH_2$—NH—CO—$CH_2$—N(—$CH_2$—$CH_2$—OH)$SO_2$-β

α-$CH_2$—NHCO—$(CH_2)_{10}$—S—$CH_2CH_2$-β

α-$CH_2NHCOCH_2$—O—$CH_2CH_2$-β

α-$CH_2NHCO(CH_2)_{10}$—O—$CH_2CH_2$-β

α-$CH_2$—$C_6H_4$—O—$CH_2CH_2$-β

α-$CH_2$—O—$CH_2$—C($CH_2$—$OCH_2CH_2$—$C_6F_{13}$)$_2$—$CH_2$—$OCH_2$—$CH_2$-β

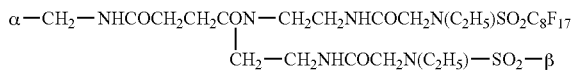

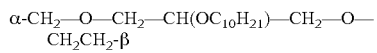

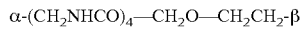

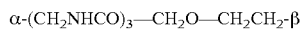

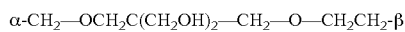

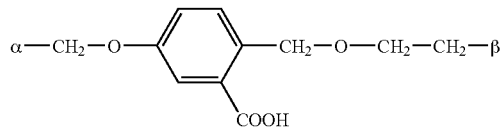

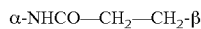

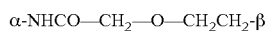

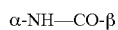

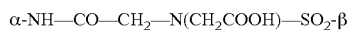

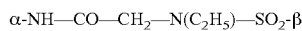

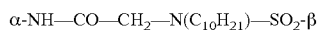

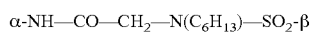

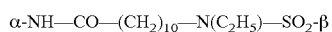

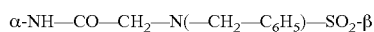

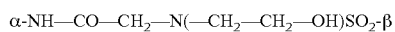

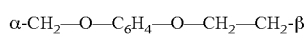

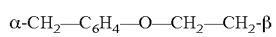

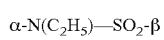

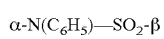

and in which α represents the binding site to the complexing agent or metal complex K, and β represents the binding site to the fluorine radical, are used.

Aspect 10 is the use according to aspects 8 and/or 9, wherein the compounds of formula I in which n in formula $—C_nF_{2n}E$ stands for numbers 4-15 and/or E in this formula means a fluorine atom are used.

Aspect 11 is the use according to one of aspects 8 to 10, wherein the following compounds are used:

Gadolinium complex of 10-[1-methyl-2-oxo-3-aza-5-oxo-{4-perfluorooctylsulfonyl-piperazin-1-yl}-pentyl]-1,4,7-tris(carboxymethyl)-1,4,7,10-tetraazacyclododecane, Gadolinium complex of 10-[2-hydroxy-4-aza-5-oxo-7-oxa-10,10,11,11,12,12,13,13,14,14,15,15,16,16,17,17-heptadecafluoroheptadecyl]-1,4,7-tris(carboxymethyl)-1,4,7,10-tetraazacyclododecane, Gadolinium complex of 10-[2-hydroxy-4-aza-5,9-dioxo-9-{4-perfluorooctyl)-piperazin-1-yl}-nonyl]-1,4,7-tris(carboxymethyl)-1,4,7,10-tetraazacyclododecane, Gadolinium complex of 10-[2-hydroxy-4-aza-5-oxo-7-aza-7-(perfluorooctyl-sulfonyl)-nonyl]-1,4,7-tris(carboxymethyl)-1,4,7,10-tetraazacyclododecane, Gadolinium complex of 10-[2-hydroxy-4-oxa-1H,1H,2H,3H,3H,5H,5H,6H,6H-perfluorotetradecyl]-1,4,7-tris(carboxymethyl)-1,4,7,10-tetraazacyclododecane, Gadolinium complex of 10-[2-hydroxy-4-aza-5-oxo-7-oxa-10,10,11,11,12,12,13,13,14,14,15,15,16,16,17,17,18,18,19,19-henicosafluoro-nonadecyl]-1,4,7-tris(carboxymethyl)-1,4,7,10-tetraazacyclododecane, Gadolinium complex of 10-[2-hydroxy-4-aza-5-oxo-11-aza-11-(perfluorooctylsulfonyl)-tridecyl]-1,4,7-tris(carboxymethyl)-1,4,7,10-tetraazacyclododecane, Gadolinium complex of 10-[2-hydroxy-4-aza-5-oxo-7-aza-7-(perfluorooctylsulfonyl)-8-phenyl-octyl]-1-4-7-tris(carboxymethyl)-1,4,7,10-tetraaza-cyclododecane.

In another embodiment of this invention, those compounds of general formula Ia according to aspects 12 to 21 are used as preferred compounds. These compounds are known and are described in WO 99/01161. Their use as MRI contrast media for visualization of thrombi still had not been described to date. Of these compounds, quite especially preferably metal complex MK 12 (cf. Table 1) is used.

Aspect 12 is the use according to the invention, wherein as perfluoroalkyl-containing metal complexes, the compounds of general formula Ia are used $$A\text{-}R^F \qquad (Ia)$$

in which

A is a molecule part that contains 2 to 6 metal complexes, which are bonded directly or via a linker to a nitrogen atom of an annular skeleton chain, and $R^F$ is a perfluorinated, straight-chain or branched carbon chain with formula $—C_nF_{2n}E$, in which E represents a terminal fluorine, chlorine, bromine, iodine or hydrogen atom, and n stands for numbers 4-30, whereby molecule part A has the following structure:

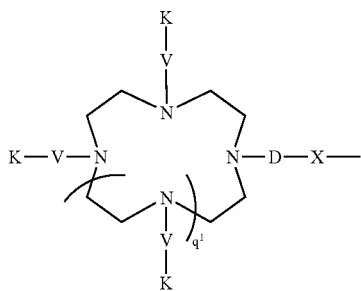

whereby $q^1$ is a number 0, 1, 2 or 3,

K stands for a complexing agent or metal complex or their salts of organic and/or inorganic bases or amino acids or amino acid amides, X is a direct bond to the perfluoroalkyl group, a phenylene group or a $C_1$-$C_{10}$-alkylene chain, which optionally contains 1-15 oxygen atoms, 1-5 sulfur atoms, 1-10 carbonyl groups, 1-10 ($NR^d$) groups, 1-2 $NR^dSO_2$ groups, 1-10 $CONR^d$ groups, 1 piperidine group, 1-3 $SO_2$ groups and 1-2 phenylene groups or optionally is substituted by 1-3 radicals $R^F$, in which $R^d$ stands for a hydrogen atom, a phenyl group, benzyl group or a $C_1$-$C_{15}$ alkyl group, which optionally contains 1-2 NHCO groups, 1-2 CO groups, or 1-5 oxygen atoms and optionally is substituted by 1-5 hydroxy, 1-5 methoxy, 1-3 carboxy, or 1-3 $R^F$ radicals, V is a direct bond or a chain of general formula IIa or IIIa:

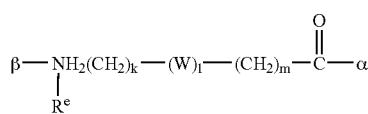

(IIa)

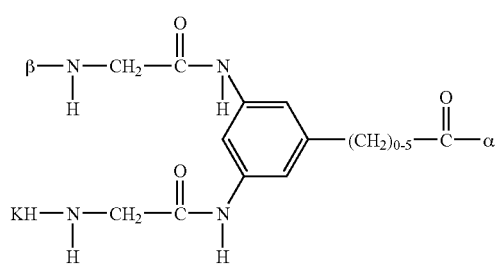

(IIIa)

in which $R^e$ is a hydrogen atom, a phenyl group, a benzyl group or a $C_1$-$C_7$-alkyl group, which optionally is substituted with a carboxy group, a methoxy group or a hydroxy group, W is a direct bond, a polyglycol ether group with up to 5 glycol units, or a molecule part of general formula IVa —CH($R^h$)            (IVa)

in which $R^h$ is a $C_1$-$C_7$ carboxylic acid, a phenyl group, a benzyl group or a —$(CH_2)_{1-5}$—NH—K group, α represents the binding to the nitrogen atom of the skeleton chain, β represents the binding to complexing agents or metal complex K, and in which variables k and m stand for natural numbers between 0 and 10, and l stands for 0 or 1 and whereby

D is a CO or $SO_2$ group, are used,

Aspect 13 is the use according to aspect 12, wherein the compounds of general formula Ia in which q is the number 1 are used.

Aspect 14 is the use according to aspect 12, wherein the compounds of general formula Ia are used, in which molecule part X is an alkylene chain, which contains 1-10 $CH_2CH_2O$ groups or 1-5 $COCH_2NH$ groups, a direct bond or one of the following structures

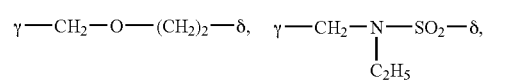

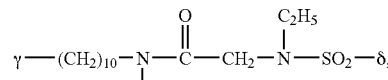

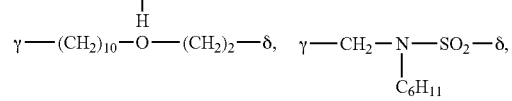

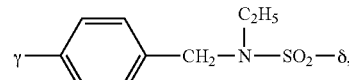

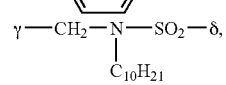

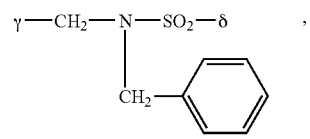

whereby

γ binds to D, and δ binds to $R^F$.

Aspect 15 is the use according to aspect 12, wherein the compounds of general formula Ia, in which V is a molecule part with one of the following structures

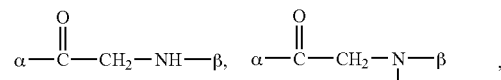

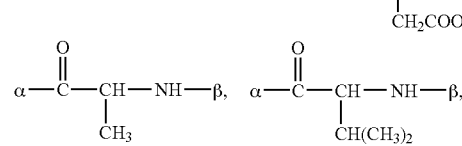

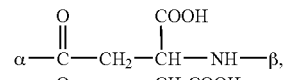

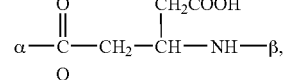

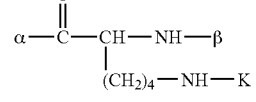

are used.

Aspect 16 is the use according to aspect 12, wherein the compounds of general formula Ia, in which K represents a complex of general formula Va, VIa, VIIa or VIIIa,

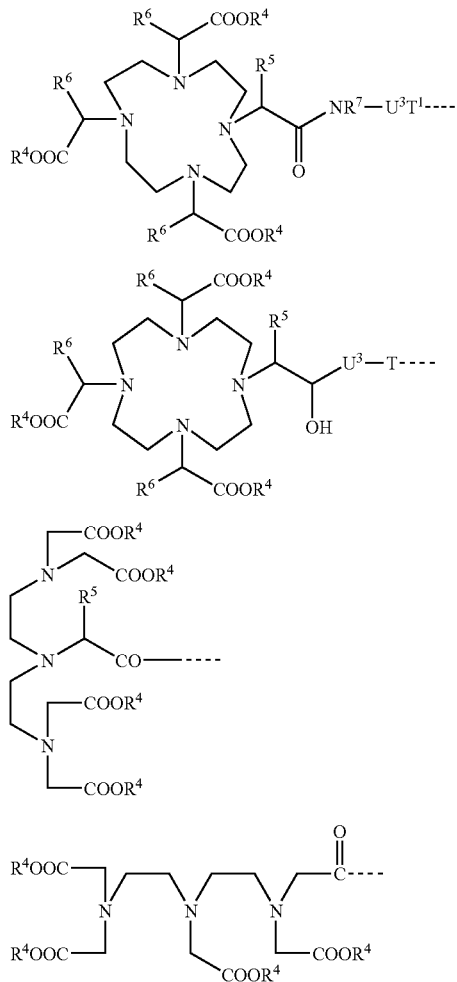

are used,
whereby
- $R^4$, independently of one another, are a hydrogen atom or a metal ion equivalent of the elements of atomic numbers 23-29, 42-46 or 58-70.
- $R^5$ is a hydrogen atom or a straight-chain, branched, saturated or unsaturated $C_1$-$C_{30}$ alkyl chain, which optionally is substituted by 1-5 hydroxy, 1-3 carboxy or 1 phenyl group(s) and/or optionally is interrupted by 1-10 oxygen atoms, 1 phenylene group or 1 phenylenoxy group,
- $R^6$ is a hydrogen atom, a straight-chain or branched $C_1$-$C_7$ alkyl radical, a phenyl radical or a benzyl radical,
- $R^7$ is a hydrogen atom, a methyl group or ethyl group, which optionally is substituted by a hydroxy group or carboxy group,
- $U^3$ is a straight-chain, branched, saturated or unsaturated $C_1$-$C_{20}$ alkylene group optionally containing 1-5 imino groups, 1-3 phenylene groups, 1-3 phenylenoxy groups, 1-3 phenyleniminogroups, 1-5 amide groups, 1-2 hydrazide groups, 1-5 carbonyl groups, 1-5 ethylenoxy groups, 1 urea group, 1 thiourea group, 1-2 carboxyalkylimino groups, 1-2 ester groups, 1-1-0 oxygen atoms, 1-5 sulfur atoms and/or 1-5 nitrogen atoms, and/or optionally substituted by 1-5 hydroxy groups, 1-2 mercapto groups, 1-5 oxo groups, 1-5 thioxo groups, 1-3 carboxy groups, 1-5 carboxyalkyl groups, 1-5 ester groups and/or 1-3 amino groups, whereby the optionally contained phenylene groups can be substituted by 1-2 carboxy groups, 1-2 sulfone groups or 1-2 hydroxy groups
- $T^1$ stands for a —CO-β, —NHCO-β or —NHCS-β group, whereby β represents the binding site to V.

Aspect 17 is the use according to aspect 16, wherein the $C_1$-$C_{20}$-alkylene chain that stands for $U^3$ contains the groups —$CH_2NHCO$—, —$NHCOCH_2O$—, —$NHCOCH_2OC_6H_4$—, —$N(CH_2CO_2H)$—, —$CH_2OCH_2$—, —$NHCOCH_2C_6H_4$—, —$NHCSNHC_6H_4$—, —$CH_2OC_6H_4$—, —$CH_2CH_2O$— and/or is substituted by the groups —COOH and —$CH_2COOH$.

Aspect 18 is the use according to aspect 16, wherein $U^3$ stands for a —$CH_2$—, —$CH_2CH_2$—, —$CH_2CH_2CH_2$—, —$C_6H_4$—, —$C_6H_{10}$—, —$CH_2C_6H_4$—, —$CH_2NHCOCH_2CH(CH_2CO_2H)$—$C_6H_4$—, —$CH_2NHCOCH_2OCH_2$—, or —$CH_2NHCOCH_2C_6H_4$— group.

Aspect 19 is the use according to aspect 12, wherein the compounds of general formula Ia in which K has one of the following structures:

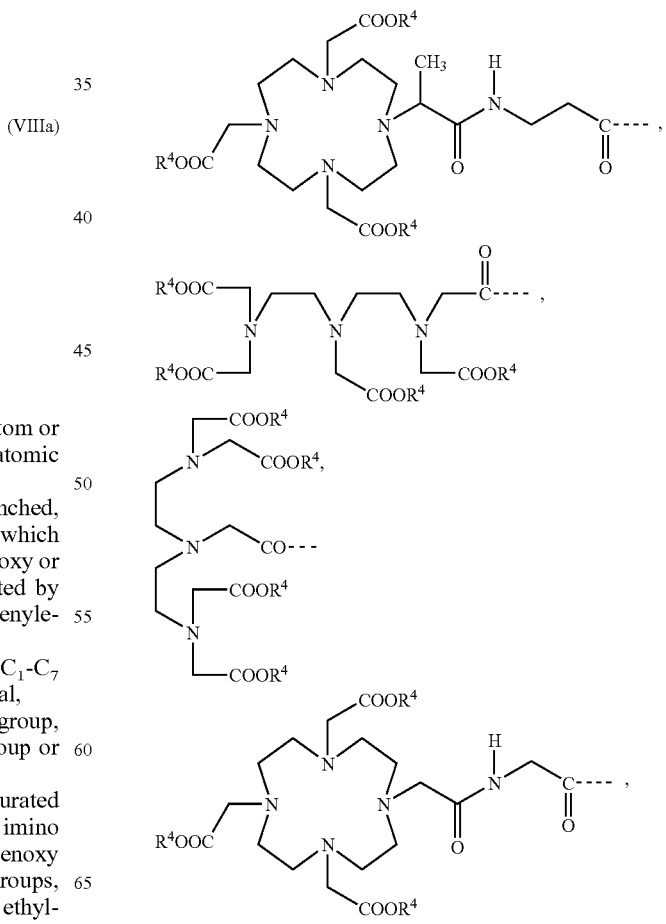

-continued

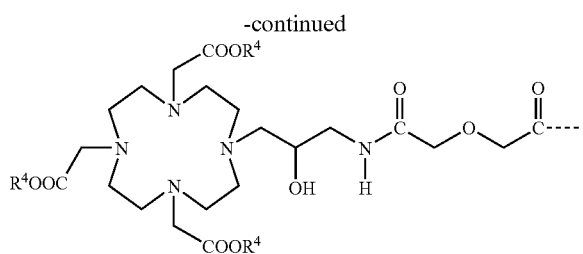

are used.

Aspect 20 is the use according to one of aspects 12 to 19, wherein the compounds of general formula Ia in which the perfluoroalkyl chain $R^F$ is —$C_6F_{13}$, —$C_8F_{17}$, —$C_{10}F_{21}$ or —$C_{12}F_{25}$ are used.

Aspect 21 is the use according to one of aspects 12 to 20, wherein the gadolinium complex of 1,4,7-tris{1,4,7-tris(N-(carboxylatomethyl)-10-[N-1-methyl-3,6-diaza-2,5,8-trioxooctane-1,8-diyl)]-1,4,7,10-tetraazacyclododecane, Gd complex}-10-[N-2H,2H,4H,4H,5H,5H-3-oxa-perfluorotridecanoyl]-1,4,7,10-tetraazacyclododecane is used.

In another preferred embodiment of the invention, the macrocyclic perfluroalkyl compounds of general formula Ib

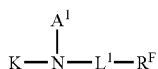
(Ib)

in which
K means a complexing agent or a metal complex of general formula IIb

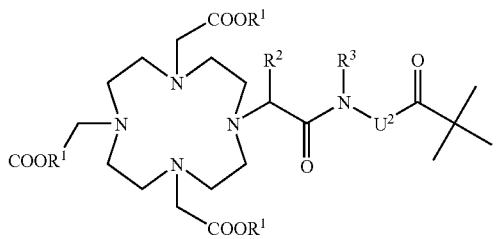
(IIb)

whereby
$R^1$ stands for a hydrogen atom or a metal ion equivalent of atomic numbers 23-29, 42-46 or 58-70,
$R^2$ and $R^3$ stand for a hydrogen atom, a $C_1$-$C_7$ alkyl group, a benzyl, group, a phenyl group, —$CH_2OH$ or —$CH_2$—$OCH_3$, and
$U^2$ stands for radical $L^1$, whereby $L^1$ and $U^2$, independently of one another, can be the same or different,
$A^1$ means a hydrogen atom, a straight-chain or branched $C_1$-$C_{30}$ alkyl group, which optionally is interrupted by 1-15 oxygen atoms, and/or optionally is substituted with 1-10 hydroxy groups, 1-2 COOH groups, a phenyl group, a benzyl group and/or 1-5 —$OR^9$ groups, with $R^9$ in the meaning of a hydrogen atom or a $C_1$-$C_7$ alkyl radical, or -$L^1$-$R^F$,
$L^1$ means a straight-chain or branched $C_1$-$C_{30}$-alkylene group, which optionally is interrupted by 1-10 oxygen atoms, 1-5 —NH—CO groups, 1-5 —CO—NH groups, by a phenylene group optionally substituted by a COOH group, 1-3 sulfur atoms, 1-2 —N($B^1$)—$SO_2$ groups and/or 1-2 —$SO_2$—N($B^1$) groups with $B_1$ in the meaning of $A^1$, an NHCO group, a CONH group, an N($B_1$)—$SO_2$ group or an —$SO_2$—N($B^1$) group and/or optionally is substituted with radical $R^F$, and
$R^F$ means a straight-chain or branched perfluorinated alkyl radical of formula $C_nF_{2n}E$, whereby n stands for numbers 4-30, and
E stands for a terminal fluorine atom, chlorine atom, bromine atom, iodine atom or a hydrogen atom,
and optionally present acid groups optionally can be present as salts of organic and/or inorganic bases or amino acids or amino acid amides, as they and their production are disclosed and defined in WO 02/13874,
can be used.

According to the invention, metal complexes MK 17, MK 18, MK 19, MK 21, and MK 23 (cf. Table 1) are quite especially preferably used.

These compounds of general formula Ib are very well suited as MRI contrast media for visualizing thrombi.

In another preferred embodiment of the invention, the perfluoroalkyl-containing complexes with sugar radicals of general formula Ic (see WO 02/13874)

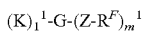

(Ic)

in which
R represents a mono-or oligosaccharide radical bonded by the 1-OH— or 1-SH-position,
$R^F$ is a perfluorinated, straight-chain or branched carbon chain with the formula —$C_nF_{2n}E$, in which E represents a terminal fluorine, chlorine, bromine, iodine or hydrogen atom, and n stands for numbers 4-30,
K stands for a metal complex of general formula IIc,

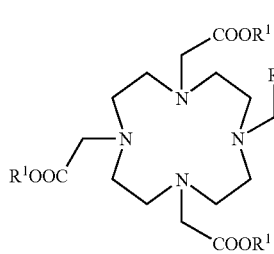
(IIc)

in which
$R^1$ means a hydrogen atom or a metal ion equivalent of atomic numbers 23-29, 42-46 or 58-70,
provided that at least two $R^1$ stand for metal ion equivalents,
$R^2$ and $R^3$, independently of one another, represent hydrogen, $C_1$-$C_7$ alkyl, benzyl, phenyl, —$CH_2OH$ or —$CH_2OCH_3$, and
U represents —$C_6H_4$—O—$CH_2$-ω, —$(CH_2)_{1-5}$-ω, a phenylene group, —$CH_2$—NHCO—$CH_2$—CH($CH_2COOH$)—$C_6H_4$-ω, —$C_6H_4$—$(OCH_2CH_2)_{0-1}$—N($CH_2COOH$)—$CH_2$-ω, or a $C_1$-$C_{12}$ alkylene group or $C_7$-$C_{12}$—$C_6H_4$—O group optionally interrupted by one or more oxygen atoms, 1 to 3 —NHCO groups or 1 to 3 —CONH groups and/or substituted with 1 to 3 —(CH$_2$)$_{0-5}$ COOH groups, whereby ω stands for the binding site to —CO—,
or
of general formula IIIc

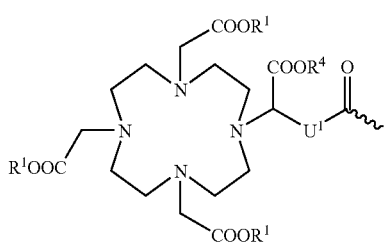
(IIIc)

in which R$^1$ has the above-mentioned meaning, R$^4$ represents hydrogen or a metal ion equivalent mentioned under R$^1$, and U$^1$ represents —C$_6$H$_4$—O—CH$_2$-ω, whereby ω means the binding site to —CO—,
or of general formula IVc

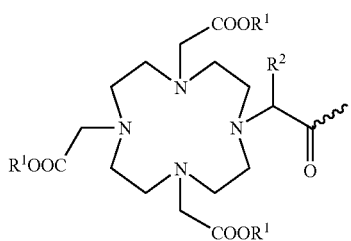
(IVc)

in which R$^1$ and R$^2$ have the above-mentioned meaning
or of general formula VcA or VcB

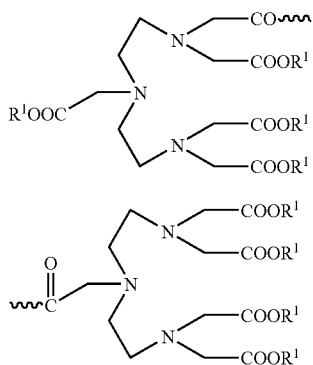
(VcA)

(VcB)

in which R$^1$ has the above-mentioned meaning,
or of general formula VIc

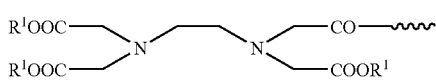
(VIc)

in which R$^1$ has the above-mentioned meaning, or of general formula VIIc

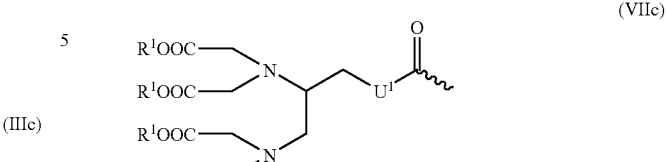
(VIIc)

in which R$^1$ has the above-mentioned meaning, and
U$^1$ represents —C$_6$H$_4$—O—CH$_2$—CO, whereby ω means the binding site to —CO—
or of general formula VIIIc

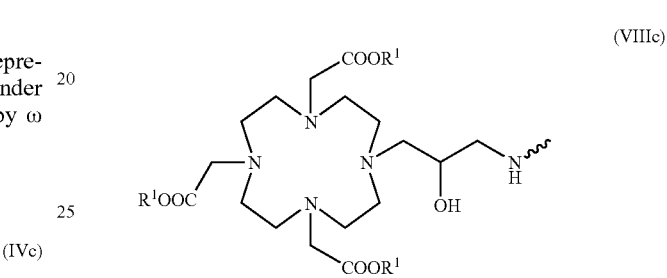
(VIIIc)

in which R$^1$ has the above-mentioned meaning,
and in radical K, optionally present free acid groups optionally can be present as salts of organic and/or inorganic bases or amino acids or amino acid amides,
G for the case that K means metal complexes IIc to VIIc, represents a radical that is functionalized in at least three places and is selected from the following radicals a) to j)

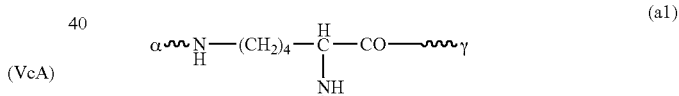
(a1)

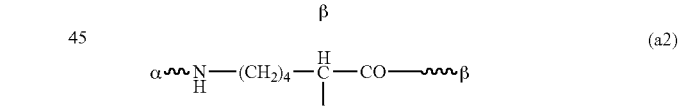
(a2)

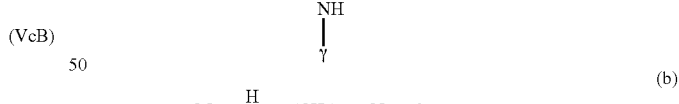
(b)

(c)

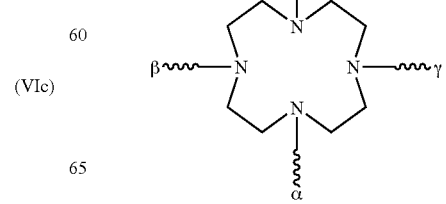

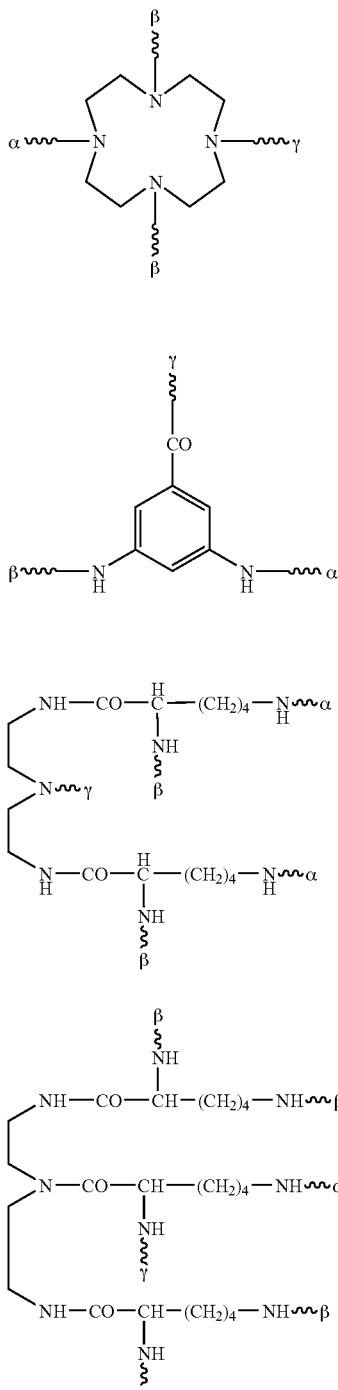

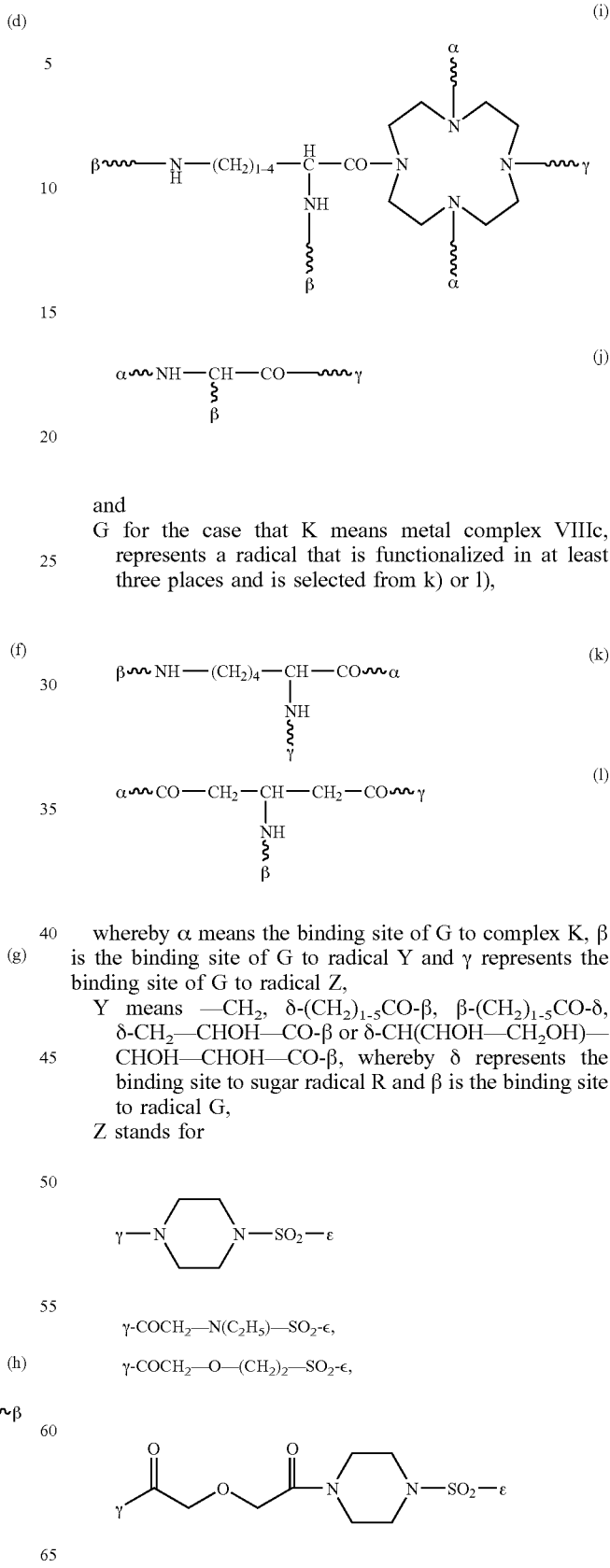

and

G for the case that K means metal complex VIIIc, represents a radical that is functionalized in at least three places and is selected from k) or l), whereby α means the binding site of G to complex K, β is the binding site of G to radical Y and γ represents the binding site of G to radical Z, Y means —CH$_2$, δ-(CH$_2$)$_{1-5}$CO-β, β-(CH$_2$)$_{1-5}$CO-δ, δ-CH$_2$—CHOH—CO-β or δ-CH(CHOH—CH$_2$OH)—CHOH—CHOH—CO-β, whereby δ represents the binding site to sugar radical R and β is the binding site to radical G, Z stands for or

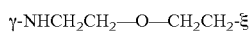

whereby γ represents the binding site of Z to radical G, and ξ means the binding site of Z to perfluorinated radical $R^F$ and $l^1$, $m^1$, independently of one another, mean integers 1 or 2, and $p^1$ means integers 1 to 4, can be used.

As quite especially preferred compounds of general formula Ic, metal complex MK 13 of Table 1 according to the invention is used.

In another preferred embodiment of the invention, the perfluoroalkyl-containing complexes with polar radicals of general formula Id (see WO 02/13874) are used

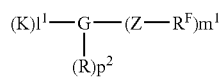
(Id)

in which $R^F$ is a perfluorinated, straight-chain or branched carbon chain with formula —$C_nF_{2n}$E, in which E represents a terminal fluorine, chlorine, bromine, iodine or hydrogen atom, and n stands for numbers 4-30, K stands for a metal complex of general formula IId,

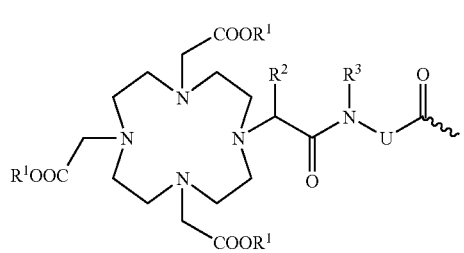
(IId)

in which $R^1$ means a hydrogen atom or a metal ion equivalent of atomic numbers 23-29, 42-46 or 58-70,
  provided that at least two $R^1$ stand for metal ion equivalents, $R^2$ and $R^3$, independently of one another, represent hydrogen, $C_1$-$C_7$ alkyl, benzyl, phenyl, —$CH_2OH$ or —$CH_2OCH_3$, and U represents —$C_6H_4$—O—$CH_2$-ω-, —$(CH_2)_{1-5}$-ω, a phenylene group, —$CH_2$—NHCO—$CH_2$—CH($CH_2COOH$)—$C_6H_4$-ω-, —$C_6H_4$—$(OCH_2CH_2)_{0-1}$—N($CH_2COOH$)—$CH_2$-ω, or a $C_1$-$C_{12}$ alkylene group or $C_7$-$C_{12}$—$C_6H_4$—O group optionally interrupted by one or more oxygen atoms, 1 to 3 —NHCO groups, 1 to 3 —CONH groups and/or substituted with 1 to 3 —$(CH_2)_{0-5}COOH$ groups, whereby ω stands for the binding site to —CO—, or of general formula IIId

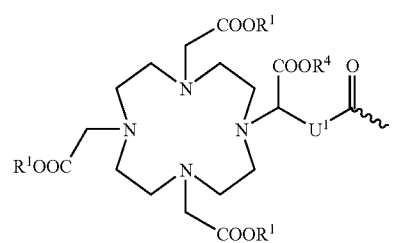
(IIId)

in which $R^1$ has the above-mentioned meaning, $R^4$ represents hydrogen or a metal ion equivalent mentioned under $R^1$, and $U^1$ represents —$C_6H_4$—O—$CH_2$-ω-, whereby ω means the binding site to —CO—, or of general formula IVd

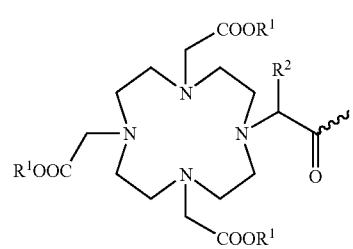
(IVd)

in which $R^1$ and $R^2$ have the above-mentioned meaning, or of general formula VdA or VdB

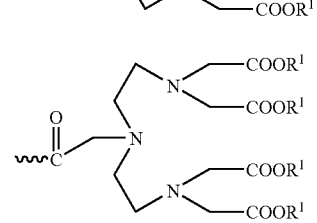
(VdA)

(VdB)

in which $R^1$ has the above-mentioned meaning, or of general formula VId

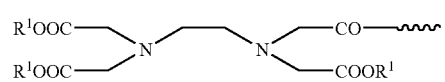
(VId)

in which $R^1$ has the above-mentioned meaning, or of general formula VIId

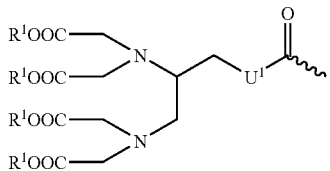
(VIId)

in which R¹ has the above-mentioned meaning, and

U¹ represents —C$_6$H$_4$—O—CH$_2$-ω-, whereby ω means the binding site to —CO—, and in radical K, optionally present free acid groups optionally can be present as salts of organic and/or inorganic bases or amino acids or amino acid amides, G represents a radical that is functionalized in at least three places and is selected from the following radicals a) to i)

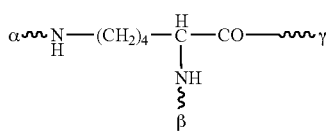
(a1)

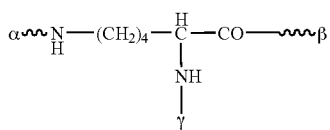
(a2)

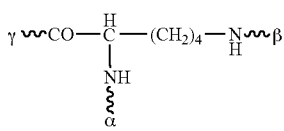
(b)

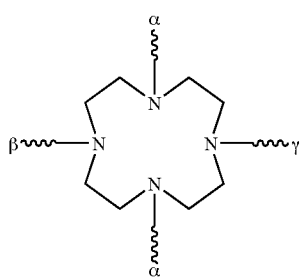
(c)

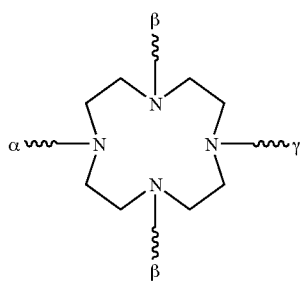
(d)

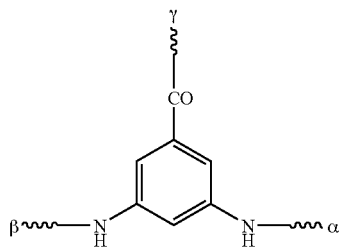
(e)

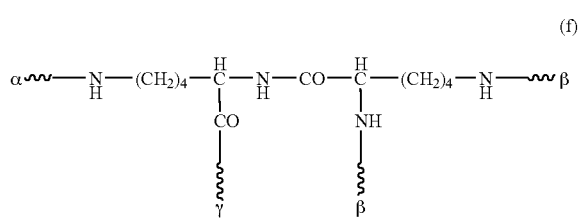
(f)

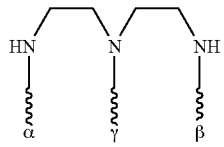
(g)

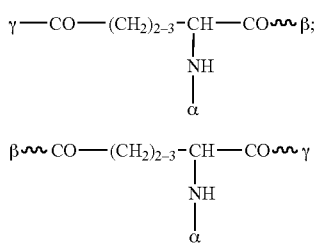
(h)

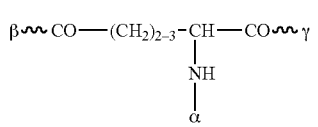
(i)

whereby α means the binding site of G to complex K, β is the binding site of G to radical R, and γ represents the binding site of G to radical Z Z stands for

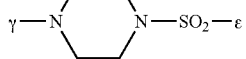

γ-C(O)CH$_2$O(CH$_2$)$_2$-ε, whereby γ represents the binding site of Z to radical G and ξ means the binding site of Z to perfluorinated radical R$^F$, R represents a polar radical that is selected from complexes K of general formulas IId to VIId, whereby R¹ here means a hydrogen atom or a metal ion equivalent of atomic numbers 20, 23-29, 42-46 or 58-70, and radicals R², R³, R⁴, U and U¹ have the above-mentioned meaning, or the folic acid radical or means a carbon chain with 2-30 C atoms that is bonded to radical G via —CO— or SO$_2$— or a direct bond to radical G, and is straight or branched, saturated or unsaturated, optionally interrupted by 1-10 oxygen atoms, 1-5 —NHCO groups, 1-5 —CONH groups, 1-2 sulfur atoms, 1-5 —NH groups or 1-2 phenylene groups, which optionally can be substituted with 1-2 OH groups, 1-2 $NH_2$ groups, 1-2 —COOH groups, or 1-2 —$SO_3H$ groups, or optionally substituted with 1-8 OH groups, 1-5 —COOH groups, 1-2 $SO_3H$ groups, 1-5 $NH_2$ groups, 1-5 $C_1$-$C_4$ alkoxy groups, and $l^1$, $m^1$, $p^2$, independently of one another, mean integers 1 or 2.

Especially preferred compounds of general formula Id are those with macrocyclic compound K of general formulas IId, IIId, VdB or VIId.

Metal complex MK 12 of Table 1 according to the invention is used as a quite especially preferred compound of general formula Id.

In another preferred embodiment of the invention, galenical formulations can be used that contain paramagnetic and diamagnetic perfluoroalkyl-containing substances. The paramagnetic and diamagnetic substances are preferably present in a dissolved state in an aqueous solvent.

As paramagnetic, perfluoroalkyl-containing compounds, all above-mentioned metal complexes of general formulas I, Ia, Ib, Ic and/or Id according to the invention can be used in the formulations.

The diamagnetic perfluoroalkyl-containing substances are those of general formula XX (see WO 02/13874):

$$R^F\text{-}L^2\text{-}B^2 \qquad (XX)$$

in which $R^F$ represents a straight-chain or branched perfluoroalkyl radical with 4 to 30 carbon atoms, $L^2$ stands for a linker and $B^2$ stands for a hydrophilic group. Linker $L^2$ is a direct bond, an —$SO_2$ group, or a straight-chain or branched carbon chain with up to 20 carbon atoms, which can be substituted with one or more —OH, —COO, —$SO_3$ groups and/or optionally contains one or more —O—, —S—, —CO—, —CONH—, —NHCO—, —$CONR^9$—, —$NR^9CO$—, —$SO_2$—, —$PO_4$—, —NH— or —$NR^9$ groups, an aryl ring or a piperazine, whereby $R^9$ stands for a $C_1$ to $C_{20}$ alkyl radical, which in turn can contain one or more O atoms, and/or can be substituted with —COO⁻ or $SO_3$ groups.

Other suitable diamagnetic perfluoroalkyl-containing compounds are conjugates that consist of cyclodextrin and perfluoroalkyl-containing compounds. These conjugates consist of α-, β- or γ-cyclodextrin and compounds of general formula XXII (see WO 02/13874)

$$A^1\text{-}L^3\text{-}R^F \qquad (XXII)$$

in which $A^1$ stands for an adamantan, biphenyl or anthracene molecule, $L^3$ stands for a linker, and $R^F$ stands for a straight-chain or branched perfluoroalkyl radical with 4 to 30 carbon atoms. Linker $L^3$ is a straight-chain hydrocarbon chain with 1 to 20 carbon atoms, which can be interrupted by one or more oxygen atoms, one or more CO—, $SO_2$—, CONH—, NHCO—, CONR—, NRCO—, NH— or NR groups or a piperazine, whereby R is a $C_1$-$C_5$ alkyl radical.

In summary, it has been determined that as quite especially preferred compounds, gadolinium complexes MK 1-30 that are presented in Table 1 meet the criteria according to the invention. The physical parameters of these metal complexes are presented in Table 1.

Both the paramagnetic compounds of general formulas I, Ia, Ib, Ic and Id according to the invention and the formulations that consist of paramagnetic and diamagnetic perfluoroalkyl-containing substances according to the invention are extremely well suited as contrast media in MR-imaging for visualization of thrombi.

TABLE 1

Metal Complexes (MK) that are Quite Especially Preferably Used According to the Invention, Their Origin and Their Physicochemical Parameters

| Komplex | Herkunft | Beispiel Nr. | $R^1$ [l: mmol · s] | CMC [mol/l] | 2 Rh [nm] |
|---|---|---|---|---|---|
| MK 1 | WO 99/01161 | 18 | 23.0 | 1.5 · 10⁻⁴ | 3.5 |
| MK 2 | WO 97/26017 | 1 | 29.7 | 1.0 · 10⁻⁵ | 31.5 |
| MK 3 | WO 97/26017 | 2 | 33.0 | 2.3 · 10⁻⁵ | 14.0 |
| MK 4 | WO 97/26017 | 3 | 27.5 | 1.44 · 10⁻⁵ | 3.2 |
| MK 5 | WO 99/01161 | 25 | 15.1 | 3.1 · 10⁻⁵ | 7.0 |
| MK 6 | WO 97/26017 | 31 | 26.0 | 9.8 · 10⁻⁴ | 4.3 |
| MK 7 | WO 99/01161 | 12 | 21.4 | 1.81 · 10⁻⁶ | 4.2 |
| MK 8 | WO 97/26017 | 33 | 35.7 | 1.86 · 10⁻⁶ | 4.6 |
| MK 9 | WO 97/26017 | 35 | 34.0 | 3.25 · 10⁻⁶ | 4.3 |
| MK 10 | WO 97/26017 | 34 | 24.9 | 7.06 · 10⁻⁶ | 3.2 |
| MK 11 | WO 97/26017 | 32 | 24.8 | 2.88 · 10⁻⁶ | 35.5 |
| MK 12 | WO 99/01161 | 1 | 19.5 | 8.9 · 10⁻⁴ | 2.2 |
| MK 13 | WO 02/13874 | 21 | 15.9 | 2.5 · 10⁻⁶ | 4.4 |
| MK 14 | WO 02/13874 | 54 | 21.3 | 3.9 · 10⁻⁵ | 4.9 |
| MK 15 | WO 99/01161 | 14 | 19.3 | 8.7 · 10⁻⁶ | 3.2 |
| MK 16 | WO 00/56723 | 7 | 21.0 | 2.8 · 10⁻⁶ | 4.3 |
| MK 17 | WO 02/13874 | 6 | 13.3 | 2.65 · 10⁻⁶ | 6.0 |
| MK 18 | WO 02/13874 | 2 | 19.6 | 3.9 · 10⁻⁶ | 4.4 |
| MK 19 | WO 02/13874 | 5 | 30.3 | 5.2 · 10⁻⁵ | 3.0 |
| MK 20 | WO 00/56723 | 4 | 21.9 | 4.6 · 10⁻⁵ | 5.5 |
| MK 21 | WO 02/13874 | 3 | 21.2 | 2.92 · 10⁻⁵ | 2.5 |
| MK 22 | WO 00/56723 | 7 | 27.8 | 4.4 · 10⁻⁶ | 5.7 |
| MK 23 | WO 02/13874 | 1 | 25.7 | 7.9 · 10⁻⁶ | 5.4 |
| MK 24 | WO 99/01161 | 1 | 13.9 | 6.3 · 10⁻⁶ | 10.0 |
| MK 25 | WO 99/01161 | 5 | 21.3 | 1.4 · 10⁻⁴ | 3.5 |
| MK 26 | WO 02/13874 | 57 | 22.8 | 4.3 · 10⁻⁶ | 5.2 |
| MK 27 | WO 97/25017 | 38 | 30.5 | 1.07 · 10⁻⁵ | 7.4 |
| MK 28 | diese Anm. | 1 | 27.9 | 8.1 · 10⁻⁶ | 4.7 |
| MK 29 | diese Anm. | 2 | 17.7 | 7.6 · 10⁻⁵ | 4.8 |
| MK 30 | diese Anm. | 3 | 27.9 | 7.0 · 10⁻⁶ | 7.9 |

[Key to Table 1:]
Komplex = Complex
Herkunft = Origin
Beispiel Nr. = Example No.
Diese Anm. = This application
CMC: Critical Micelle Formation Concentration
2 Rh: Hydrodynamic Micelle Diameter
$R^1$: Relaxivity The measurements were carried out in plasma at 40° C. and a field strength of 0.47 Tesla.

EXAMPLE 1 a) 6-Benzyloxycarbonyl-2-N-2H,2H,4H,4H,5H,5H-3-oxa-perfluorotridecanoyl-L-lysine methyl ester 2 drops of dimethylformamide are added to the solution of 50 g (95.8 mmol) of 2H,2H,4H,4H,5H,5H-3-oxaperfluorotridecanoic acid (produced from 2H,2H,3H,3H-perfluorodecanol and bromoacetic acid-t-butyl ester with subsequent ester cleavage) in 250 ml of thionyl chloride, and it is refluxed for 5 hours. Then, it is concentrated by evaporation in a vacuum, the residue is taken up in 250 ml of dichloromethane, and the solution is added in drops at 0° C. while being stirred to the solution of 34.74 g (105.0 mmol) of 6-N-benzyloxycarbonyl-L-lysine-methyl ester, hydrochloride (commercially available products, Bachem) as well as 46.85 ml (350 mmol) of triethylamine in 400 ml of dichloromethane. It is allowed to stir overnight, mixed with 1 liter of 2N hydrochloric acid, the organic phase is shaken out, the water phase is extracted twice with 100 ml of dichloromethane each, the solution is dried on sodium sulfate, dessicant is filtered out, and it is concentrated by evaporation in a vacuum. The crude product is purified on silica gel by chromatography. As an eluant, a mixture that consists of dichloromethane with the addition of 3% ethanol is used.

The product is obtained as a colorless gel after the concentration by evaporation.

Yield: 67.0 g (87.6% of theory) Elementary analysis:

| Cld.: | 40.61 C | 3.41 H | 40.45 F | 3.51 N |
|---|---|---|---|---|
| Fnd.: | 40.48 C | 3.54 H | 40.61 F | 3.37 N. | b) 2-N-2H,2H,4H,4H,5H,5,H-3-Oxaperfluorotridecanoyl-L-lysine methyl ester, Hydrochloride 10 g of catalyst (Pd 10%/C) is added to a solution of 63.5 g (79.5 mmol) of the title substance of Example 1a) in a mixture that consists of 500 ml of methanol and 90 ml of 1N hydrochloric acid, and it is hydrogenated until one equivalent of hydrogen is taken up at normal pressure and room temperature. Catalyst is filtered out, the latter is washed 3 times with 50 ml each of hot methanol, and the combined solutions are concentrated by evaporation. The residue is dissolved in methanol and brought to crystallization by adding diisopropyl ether.

The title compound is obtained in colorless crystals.

Yield: 55.70 g (quantitative) Elementary analysis:

| Cld.: | 32.56 C | 3.16 H | 5.06 Cl | 46.09 F | 4.00 N |
|---|---|---|---|---|---|
| Fnd.: | 32.44 C | 3.28 H | 4.95 Cl | 46.21 F | 4.11 N | c) 6-N-3,6,9,12,15-Pentaoxa-hexadecanoyl-2-N-2H,2H,4H,4H,5H,5H-3-oxa-perfluorotridecanoyl-1-lysine-methyl ester 13.31 g (50.0 mmol) of 3,6,9,12,15-pentaoxahexadecanoic acid (commercially available products) is dissolved in 100 ml of thionyl chloride, mixed with two drops of dimethylformamide and stirred overnight at room temperature. Then, it is heated for one hour to 65° C., excess thionyl chloride is removed in a rotary evaporator, and the residue is taken up in 150 ml of dichloromethane. This solution is added in drops at 0° C. to the solution of 35.04 g (50.0 mmol) of the title compound of Example 1b) and 15.18 g (150 mmol) of triethylamine in 350 ml of dichloromethane. Then, it is allowed to stir for 72 hours at room temperature. It is concentrated by evaporation, and the product is obtained by column chromatography on silica gel. As an eluant, a mixture that consists of dichloromethane/ethanol 9:1 is used. The title compound is obtained as a viscous, light yellow oil.

Yield: 37.0 g (81.1% of theory) Elementary analysis:

| Cld.: | 39.48 C | 4.53 H | 35.39 F | 3.07 N |
|---|---|---|---|---|
| Fnd.: | 39.61 C | 4.50 H | 35.50 F | 3.16 N | d) 6-N-3,6,9,12,15-Pentaoxahexadecanoyl-2-N-2H,2H,4H,4H,5H,5H-3-oxa-perfluorotridecanoyl-L-lysine 17.90 g of the title compound of Example 1c) is stirred overnight in a mixture that consists of 50 ml of methanol and 25 ml of 2N sodium hydroxide solution. It is acidified with 2N hydrochloric acid, concentrated by evaporation in a vacuum, and the residue is extracted 5 times with 50 ml each of tetrahydrofuran/ethyl acetate 2:1. The combined extracts are dried on sodium sulfate. Desiccant is filtered out, and the solution is concentrated by evaporation. The residue is purified by column chromatography on silica gel. As a mobile solvent, a mixture that consists of dichloromethane/methanol and water in a ratio of 160:40:1 is used. The title compound is obtained as a waxy, light yellow-colored residue.

Yield: 14.7 g (83.4% of theory) Elementary analysis:

| Cld.: | 38.76 C | 4.37 H | 35.94 F | 3.12 N |
|---|---|---|---|---|
| Fnd.: | 38.87 C | 4.25 H | 36.07 F | 3.21 N | e) 6-N-3,6,9,12,15-Pentaoxahexadecanoyl-2-N-2H,2H,4H,4H,5H,5H-3-oxaperfluorotridecanoyl-L-lysine-N-{1,4,7-tris[carboxylatomethyl]-1,4,7,10-tetraazacyclododecane-10-(2-hydroxy-3-yl), gadolinium complex}-amide 8.0 g (8.9 mmol) of the acid that is produced under 1d) as well as 2.05 g (17.8 mmol) of hydroxysuccinimide are dissolved in 50 ml of dimethylformamide and mixed at 0° C. with 4.60 g (22.25 mmol) of dicyclohexylcarbodiimide. It is stirred for 10 more minutes at 0° C. and then for another 2 hours at room temperature. After being cooled again to 0° C., a solution that consists of 3.93 g (6.65 mmol) of the gadolinium complex of 10-(3-amino-2-hydroxy-propyl)-1,4,7-tris-(carboxymethyl)-1,4,7,10-tetraazacyclododecane (WO 95/17451) as well as 0.58 g (13.7 mmol) of lithium chloride and 2.77 g (27.4 mmol) of triethylamine in 40 ml of dimethyl sulfoxide is added. It is allowed to stir for two days at room temperature, mixed with 650 ml of acetone, and the solution is poured onto 2 l of methyl-t-butyl ether. It is stirred for about 30 more minutes, and then solid is suctioned out. The solid is dissolved in distilled water and treated with activated carbon. The solution is filtered, concentrated by evaporation in a vacuum, and the residue is chromatographed on silica gel. As an eluant, a mixture that consists of methanol and dichloromethane is used in a 2:1 ratio.

Yield: 5.47 g (54.5% of theory) Water content: 7.3%
Elementary analysis (relative to anhydrous substance):

| Cld.: | 37.97 C | 4.71 H | 10.81 Gd | 22.19 F | 6.74 N |
|---|---|---|---|---|---|
| Fnd.: | 38.16 | 4.83 | 10.72 | 22.32 | 6.83 |

EXAMPLE 2 a) 10-(3-Carboxy-3-yl-propionic acid)-1,4,7,10-tetraazacyclododecane 150 g (761 mmol) of bromosuccinic acid is neutralized with sodium hydroxide solution (10%), and the solution is evaporated to the dry state. 65.55 g (380 mmol) of cyclene is dissolved in 300 ml of distilled water and mixed with the bisodium salt (from 150 g of bromosuccinic acid=761 mmol). It is heated to 50° C. and allowed to stir overnight. The solution is then evaporated to the dry state and co-distilled with ethanol. The residue is taken up in butanol and extracted with water. The aqueous phase is concentrated by evaporation and chromatographed on silica gel. As an eluant, mixtures that consist of methanol with ammonia (20:1-2:1) are used. The product-containing fractions are combined and evaporated to the dry state.

Yield: 54.8 g (50.4% of theory) Elementary analysis:

| Cld.: | C 50.34 | H 7.74 | N 19.57 |
|---|---|---|---|
| Fnd.: | C 50.46 | H 7.83 | N 19.69 | b) 1,4,7-Tris(carboxymethyl)-10-(3-carboxy-3-yl-propionic acid)-1,4,7,10-tetraazacyclododecane 11 g (38.14 mmol) of 10-(3-carboxy-3-yl-propionic acid)-1,4,7,10-tetraazacyclododecane is dissolved in 60 ml of distilled water and mixed with 18.03 g (190.74 mmol) of chloroacetic acid. It is then heated to 70° C., and the pH is kept between 9 and 10 by adding sodium hydroxide solution (32%). It is allowed to stir overnight at 70° C., then it is set again at a pH of 10, and 7.2 g (76.19 mmol) of chloroacetic acid is added to it. It is stirred for 3 more hours at 70° C. It is evaporated to the dry state, evaporated with methanol, taken up in methanol, and salts are filtered out. The filtrate is. concentrated by evaporation and chromatographed on an ion-exchange column Amberlite 252 C with water/ammonia as an eluant. The product-containing fractions are combined, concentrated by evaporation, taken up again in distilled water and freeze-dried. The title compound is obtained as a white foam.

Yield: 13.12 g (82.3% of theory) Water content: 9.6% Elementary analysis (relative to anhydrous substance):

| Cld.: | C 46.75 | H 6.54 | N 12.12 |
|---|---|---|---|
| Fnd.: | C 46.87 | H 6.62 | N 12.24 | c) Gadolinium complex of 10-{1-carboxy-2-carbonyl-[piperazin-1-yl-4-(perfluorooctylsulfonyl)]}-ethyl-1,4,7-tris(carboxymethyl)-1,4,7,10-tetraazacyclododecane, Sodium salt 10.0 g (16.21 mmol) of the gadolinium complex tetraazacyclododecane (produced from the ligand by complexing with gadolinium oxide) and 3.0 g of lithium chloride are dissolved while being heated slightly in 100 ml of dimethyl sulfoxide. After cooling to room temperature, 9.21 g (16.21 mmol) of perfluorooctylsulfonylpiperazine is added. Then, it is cooled to 0° C., and 12.3 g (46.63 mmol) of EEDQ (1,2-dihydro2-ethoxyquinoline-1-carboxylic acid ethyl ester) is added, and it is stirred overnight at room temperature. The reaction is poured into a mixture that consists of 800 ml of methyl-t-butyl ether and 100 ml of acetone, and it is stirred. The precipitate is purified by chromatography on silica gel. A mixture that consists of dichloromethane/methanol and ammonia in a ratio of 2:2.1 is used as an eluant. The product-containing fractions are combined and concentrated by evaporation. The residue is dissolved in 200 ml of distilled water, set at a pH of 7.2 with sodium hydroxide solution and freeze-dried. The title compound is obtained as a white foam.

Yield: 7.64 g (39% of theory) Water content: 7.8% Elementary analysis (relative to anhydrous substance):

| Cld.: | 30.31 C | 2.80 H | 27.17 F | 13.23 Gd | 7.07 N | 1.93 Na | 2.70 S |
|---|---|---|---|---|---|---|---|
| Fnd.: | 30.42 C | 2.91 H | 27.04 F | 13.29 Gd | 7.15 N | 2.04 Na | 2.59 S |

EXAMPLE 3 a) 1,4,7-Tris(carboxylatomethyl)-1,4,7,10-tetraazacyclododecane-10-[2-hydroxy-3-(N-benzyloxycarbonyltriglycidyl)-)-amino]-propyl, gadolinium complex 12.68 g (39.121 mmol) of N-benzyloxy-carbonyltriglycine (commercially available products, Bachem) is dissolved in 100 ml of dimethylformamide and mixed with 9.03 g (78.42 mmol) of N-hydroxysuccinimide. It is cooled to 0° C., and then 32.36 g (156.84 mmol) of dicyclohexylcarbodiimide is added to it. It is stirred for 20 minutes at 0° C. and then for another 3 hours at room temperature. This suspension is then added to the solution, cooled to 0° C., that consists of 15 g (26.14 mmol) of the gadolinium complex of 10-(3-amino-2-hydroxy-propyl)-1,4,7-tris(carboxymethyl)-1,4,7,10-tetraazacyclododecane (produced according to WO 95/17451) in 40 ml of distilled water and 15 ml (14 mmol) of triethylamine in 60 ml of isopropanol while being stirred. After addition is completed, it is stirred for 3 hours at room temperature. Then, urea is filtered out, it is rewashed with n-butanol and concentrated by evaporation in a vacuum. The residue is extracted several times with water. The organic phase is dried on sodium sulfate and concentrated by evaporation in a vacuum. The residue is chromatographed on silica gel. As an eluant, a mixture that consists of dichloromethane, methanol and ammonia is used. The product-containing fractions are combined, concentrated by evaporation in a vacuum, taken up again in distilled water, and subjected to freeze-drying. The title compound is obtained as a white foam.

Yield: 12.94 g (56.3% of theory) Elementary analysis:

| Cld.: | 42.36 C | 5.16 H | 17.89 Gd | 12.75 N |
|---|---|---|---|---|
| Fnd.: | 42.44 C | 5.22 H | 17.78 Gd | 12.80 N | b) 1,4,7-Tris(carboxylatomethyl)-1,4,7,10-tetraazacyclododecane-10-(2-hydroxy-3-amino-triglycidyl)-propyl, gadolinium complex In a mixture that consists of 100 ml of ethanol and 30 ml of distilled water, 8.53 g (9.7 mmol) of the title compound of Example 3a) is dissolved and mixed with 2 g of catalyst (palladium 10% on activated carbon) as well as 3 ml of acetic acid. It is hydrogenated until one equivalent of hydrogen is taken up. Then, catalyst is suctioned out, it is rewashed with ethanol, and the solution is evaporated to the dry state in a vacuum.

The title compound is obtained as a foam.

Yield: 7.22 g (quantitative) Elementary analysis:

| Cld.: | C 37.08 C | 5.28 H | 21.11 Gd | 15.04 N |
|---|---|---|---|---|
| Fnd.: | 37.21 C | 5.33 H | 21.25 Gd | 15.15 N | c) 1,4,7-Tris(carboxylatomethyl)-1,4,7,10-tetraaza-cyclododecane-10-{2-hydroxy-3-N-[triglycidyl-N-(2H,2H,4H,4H,5H,5H-3-oxa-perfluorotridecanoyl)]amino}-propyl, gadolinium complex 7.60 g (14.55 mmol) of 2H,2H,4H,4H,5H,5H-3-oxa-perfluorotridecanoic acid is dissolved in 90 ml of dimethylformamide and mixed with 3.35 g (29.1 mmol) of N-hydroxysuccinimide. It is cooled to 0° C. and then mixed with 11.71 g (56.71 mmol) of dicyclohexylcarbodiimide. After 20 minutes, the cooling is removed, and it is stirred for another 3 hours at room temperature. Then, the suspension that was produced is added while being stirred to the solution, cooled to 0° C., of 7.22 g (9.7 mmol) of the title compound of Example 3b) in a mixture that consists of 5 ml (36.7 mmol) of triethylamine, 20 ml of distilled water and 30 ml of 2-propanol. It is allowed to stir overnight at room temperature, then dicyclohexylurea is filtered out, it is rewashed with 2-propanol/distilled water 3:2 and the combined solutions are concentrated by evaporation in a vacuum. The residue is dissolved in a mixture that consists of water and butanol and extracted with butanol. The combined organic solutions are dried and concentrated by evaporation in a vacuum. The residue is purified by chromatography on silica gel. A mixture that consists of ethanol/2-propanol/concentrated ammonia in a ratio of 15:10:1 is used as an eluant. The product-containing fractions are combined, evaporated to the dry state in a vacuum, dissolved again in distilled water and freeze-dried. The title compound is obtained as a white foam.

Yield: 7.52 g (62.1% of theory) Elementary analysis:

| Cld.: | 33.66 C | 3.55 H | 25.86 F | 12.59 Gd | 8.97 N |
|---|---|---|---|---|---|
| Fnd.: | 33.55 C | 3.67 H | 25.99 F | 12.43 Gd | 9.09 N |

EXAMPLE 4

Binding to a Fibrin Gel

A coagulate (fibrin gel) forms after a 30-minute incubation time (room temperature) by mixing fibrinogen with thrombin. The latter is mixed with 0.5 ml of PBS and with 0.5 ml of a solution of the title compound of Example 21, WO 02/13874, MK 13, (0.01 and 0.1 mmol of Gd/l), and it is incubated over 16 hours at room temperature. After the supernatant is removed in the fibrin gel, the unbonded portion of the compound according to the invention is separated from fibrin by ultrafiltration (1,200 g for 30 minutes). The gadolinium content in the fibrin gel is determined by means of inductively coupled plasma-atom emissions spectroscopy (ICP-AES).

The binding of the compound according to the invention to the fibrin gel was 79.1% for the 0.01 mmol of Gd/l solution and 38.5% for the 0.1 mmol of Gd/l solution.

EXAMPLE 5

MRT Visualization (In-Vivo) of a Venous Thrombus After Intravenous Administration of the Contrast Medium in Rabbits The MR imaging was carried out in rabbits with photochemically induced thrombus (PIT). By irradiation with xenon light (540 nm, 1.100 klux, 25 minutes) after i.v. injection of rose-Bengal (20 mg/kg), the thrombus formation was induced in the left femoral vein. The blood flow in the femoral vein was controlled by means of an ultrasound probe. The imaging was carried out with a Magnetom Harmony (Siemens, 1T) before (baseline) as well as 25, 40 minutes, 1, 2, 3, 4, 24, and 48 hours after intravenous administration (about 1 hour after the thrombus induction) of 0.1 mmol of Gd/kg of the title compound of Example 21, WO 02/13874, with use of a phase contrast sequence (TR/TE=104/14 ms) as well as T1-weighted gradient echo sequences (MPRage: TR/TE/TI/α=11/4/120 ms/8°; and 3D flash: TR/TE/α=5/2 ms/50°). After the imaging, the left femoral vein (with the thrombus) was prepared outside, fixed in formalin, and stained for histological evaluation with hematoxylin/eosin (HE) or phosphotungstic acid/hematoxylin (PTAH).

In the MR imaging (MRA), the thrombus was already detectable early on (25 minutes p.i.). Images 1 and 2 that are indicated in FIG. 1 show MR images of the pelvic region 24 hours after intravenous administration of 0.1 mmol of Gd/kg of body weight of the compound according to the invention in the PIT rabbit (photochemically induced thrombus). The $T_1$-weighted 3D-flash sequence illustrates a strong signal increase in the thrombus in the area of the left femoral vein. The blood flow in the left femoral vein is considerably reduced (see MRI with phase-contrast sequence).

With both staining techniques (HE and PTAH (FIG. 2, Images 3 and 4)), the red blood clots (thrombi) could be detected in the area of the left femoral vein. The thrombi fill almost the entire lumen of the blood vessel. The exfoliation of the vascular endothelial cells and the adhesion of the thrombi is clearly visible. The intima- and adventitia nuclei have disappeared almost completely.

With this test, the suitability of the compounds according to the invention could be shown as markers for venous thrombi.

EXAMPLE 6

MRT Visualization (Ex-Vivo) of a Venous Thrombus According to Intravenous Administration of the Contrast Medium in Rabbits The MR imaging was carried out in rabbits with photochemically induced thrombus (PIT). By irradiation with xenon light (540 nm, 1.100 klux, 25 minutes) after i.v. injection of rose-Bengal (20 mg/kg), the thrombus formation was induced in the left femoral vein. 24 hours after intravenous administration (about 1 hour after the thrombus induction) of 0.1 mmol of Gd/kg of the title compound of Example 21 WO 02/13874, the animal was sacrificed, and the left femoral vein (with the thrombus) was prepared outside. The imaging of the damaged venous segment was carried out with a Magnetom Harmony (Siemens, 1T) with use of a T1-weighted spin echo sequence (TR/TE/α=300/12 ms/90°, with and without fat suppression).

The induced thrombus is clearly visible in the preparation by the color change. In addition, blood clots are also found outside of the vessel. In the ex-vivo MR imaging, a considerable enhancement of the thrombi can be observed with the T1-weighted spin echo sequence (see FIG. 3, Images 5 to 7).

EXAMPLE 7

Determination of the Gadolinium Concentration in the Thrombus After Intravenous Administration of the Contrast Medium in Rabbits The determination of content was carried out in rabbits with photochemically induced thrombus (PIT). By irradiation with xenon light (540 nm, 1,100 klux, 25 minutes) after i.v. injection of rose-Bengal (20 mg/kg), the thrombus formation was induced in the left femoral vein. 24 hours after intravenous administration (about 1 hour after the thrombus induction) of 0.1 mmol of Gd/kg of the title compound of Example 21 WO 02/13874, the animal was sacrificed, and various organs and tissues were removed to determine the Gd content: blood, femoral veins (with and without thrombus), muscle. After the tissue samples decomposed, the gadolinium concentration (ppm) was measured by means of ICP-AES.

In the left femoral vein (with thrombus), the Gd concentration was 63 ppm; however, it was only 35 ppm in the control vessel. The blood clot outside of the vessel had a high Gd content of 166 ppm. In the blood at the time of 24 hours p.i., only a Gd concentration of 15 ppm was detectable, and in the non-signal-enhanced muscle, a Gd concentration of 10 ppm was detectable.

Figure 1:
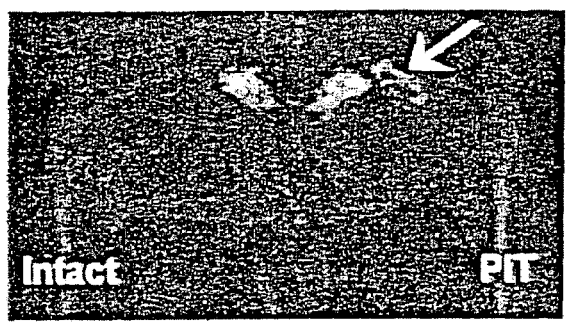
FIG. 1 illustrates images 1 and 2, which show MR images of the pelvic region 24 hours after intravenous administration of 0.1 mmol of Gd/kg of body weight of the compound according to the invention in the PIT rabbit (photochemically induced thrombus).
Figure 1:
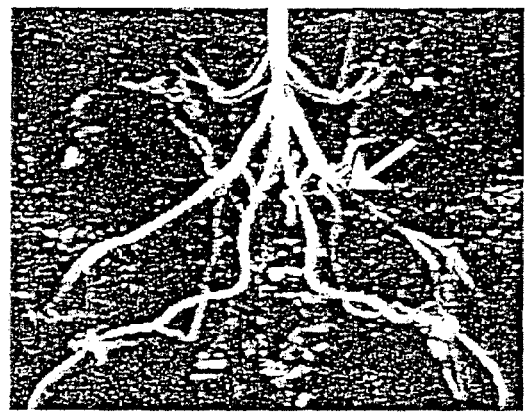
Figure 2:
FIG. 2 illustrates images 3 and 4, which show that with both staining techniques (HE and PTAH), the red blood clots (thrombi) could be detected in the area of the left femoral vein.
Figure 2:
Figure 3:
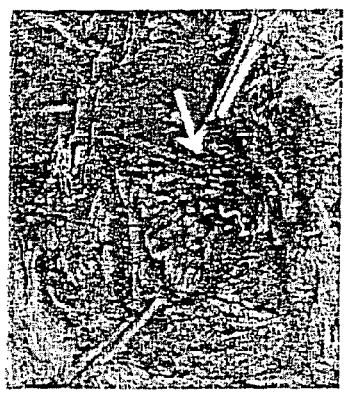
FIG. 3 illustrates images 5 and 7, which show that in the ex-vivo MR imaging, a considerable enhancement of the thrombi can be observed with the T1-weighted spin echo sequence.
Figure 3:
Figure 3:
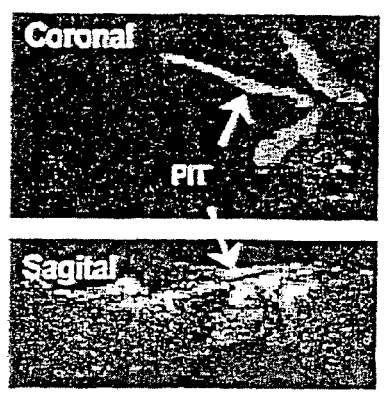

The invention claimed is:

1. A method of MR imaging for visualization of intravascular thrombi comprising administering to a subject who is to undergo MR imaging for determination of the presence of intravascular thrombi, as contrast media for visualization, perfluoroalkyl-containing metal complexes that have a critical micelle formation concentration $<10^{-3}$ mol/l, a hydrodynamic micelle diameter (2 Rh)>1 nm and a proton relaxivity in plasma $(R^1)>10$ l/mmol·s, and visualizing intravascular thrombi in said subject with an MR imaging apparatus.

2. A method according to claim 1, wherein venous thrombi is visualized.

3. A method according to claim 1, wherein arterial thrombi is visualized.

4. A method according to claim 1, wherein early determination of a thrombotic occlusive vascular disease is achieved by said visualization.

5. A method according to claim 1, wherein the metal complexes have a micelle formation concentration of $<10^{-4}$ mol/l.

6. A method according to claim 1, wherein the metal complexes have a hydrodynamic micelle diameter is $\geq 3$ nm.

7. A method according to claim 1, wherein the metal complexes have a proton relaxivity in plasma of $>13$ l/mmol·s.

8. A method according to claim 1, wherein the perfluoroalkyl-containing metal complexes are of formula I $$R^F\text{-L-K} \qquad \qquad I$$

in which $R^F$ is a perfluorinated, straight-chain or branched carbon chain with formula $-C_nF_{2n}E$, in which E represents a terminal fluorine, chlorine, bromine, iodine or hydrogen atom and n stands for numbers 4-30, L means a direct bond, a methylene group, an $-NHCO$ group, a group

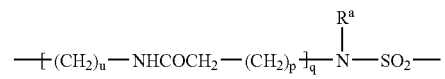

wherein p means the numbers 0 to 10, and q and u, independently of one another, mean numbers 0 or 1, and $R^a$ is a hydrogen atom, a methyl group, a benzyl group, a phenyl group, a $-CH_2OH$ group, a $CH_2OCH_3$ group, a $-CH_2-CO_2H$ group or a $C_2-C_{15}$ chain, which optionally is interrupted by 1 to 3 oxygen atoms, 1 to 2 >CO groups or an optionally substituted aryl group and/or is substituted with 1 to 4 hydroxyl groups, 1 to 2 $C_1-C_4$ alkoxy groups, 1 to 2 carboxy groups, a group $-SO_3H-$, or is a straight-chain, branched, saturated or unsaturated $C_2-C_{30}$ carbon chain, which optionally contains 1 to 10 oxygen atoms, 1 to 3 $-NR^a$ groups, 1 to 2 sulfur atoms, a piperazine, a $-CONR^a$ group, one to six $-NR^aCO$ groups, an $-SO_2$ group, an $-NR^a-CO_2$ group, 1 to 2 CO groups, a group

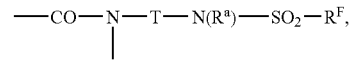

or 1 to 2 optionally substituted aryls and/or is interrupted by these groups and/or is optionally substituted with 1 to 3 $-OR^a$ groups, 1 to 2 oxo groups, 1 to 2 $-NH-COR^a$ groups, 1 to 2 $-CONHR^a$ groups, 1 to 2 $-(CH_2)_p-CO_2H$ groups, 1 to 2 groups $-(CH_2)_p-(O)_qCH_2CH_2-R^F$, wherein $R^a$, $R^F$ and p and q have the above-indicated meanings, and T means a $C_2-C_{10}$ chain, which optionally is interrupted by 1 to 2 oxygen atoms or 1 to 2 $-NHCO$ groups, K stands for a complexing agent or metal complex or a salt thereof with an organic and/or inorganic base or amino acid or amino acid amide, specifically for a complexing agent or complex of general formula II

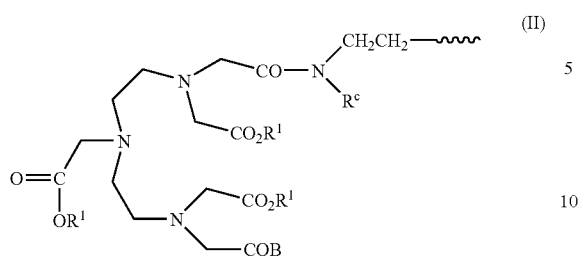

in which $R^c$, $R^1$ and B are independent of one another, and $R^c$ has the meaning of $R^a$ or means $—(CH_2)m$-L-$R^F$, wherein m is 0, 1 or 2, and L and $R^F$ have the above-mentioned meaning, $R^1$, independently of one another, mean a hydrogen atom or a metal ion equivalent of atomic numbers 22-29, 42-46 or 58-70, B means $—OR^1$ or

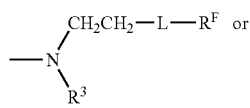

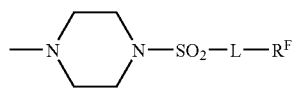

wherein $R^1$, L, $R^F$ and $R^c$ have the above-mentioned meanings, or

K stands for a complexing agent or complex of general formula III

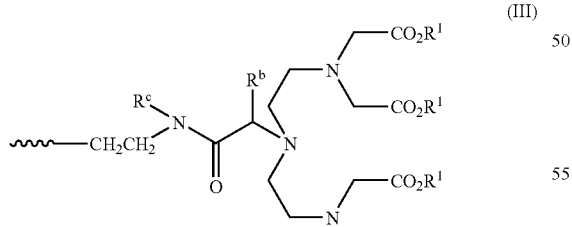

in which $R^c$ and $R^1$ have the above-mentioned meanings, $R^b$ has the meaning of $R^a$, and or K stands for a complexing agent or complex of general formula IV

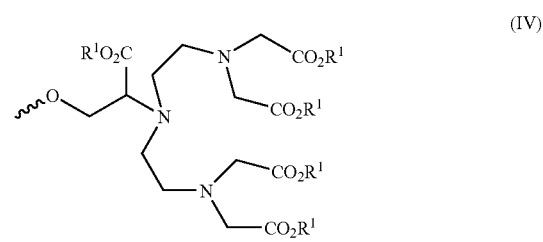

in which $R^1$ has the above-mentioned meaning or

K stands for a complexing agent or complex of general formula V

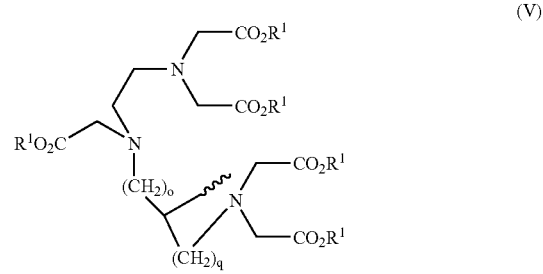

in which $R^1$ has the above-mentioned meaning, and o and q stand for numbers 0 or 1, and yields the sum o+q=1, or K stands for a complexing agent or complex of general formula VI

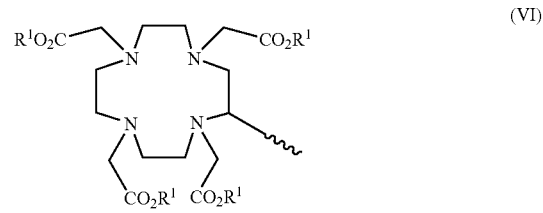

in which $R^1$ has the above-mentioned meaning or

K stands for a complexing agent or complex of general formula VII

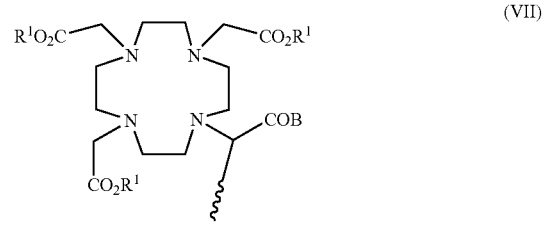

in which $R^1$ and B have the above-mentioned meanings or

K stands for a complexing agent or complex of general formula VIII

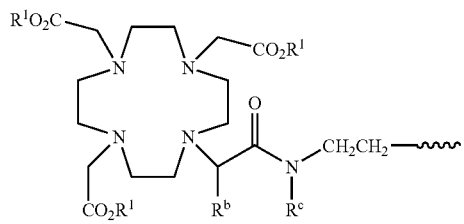

(VIII)

in which $R^c$, and $R^1$ have the above-mentioned meanings, and $R^b$ has the above-mentioned meaning of $R^a$
or
K stands for a complexing agent or complex of general formula IX

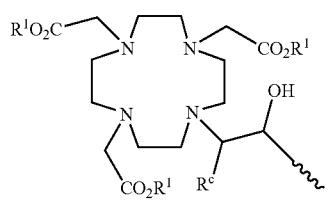

(IX)

in which $R^c$ and $R^1$ have the above-mentioned meanings,
or
K stands for a complexing agent or complex of general formula X

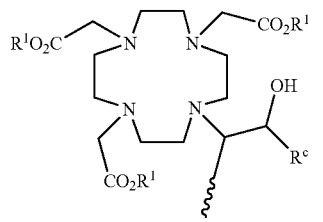

(X)

in which $R^c$ and $R^1$ have the above-mentioned meanings,
or
K stands for a complexing agent or complex of general formula XI in which $R^1$, p and q have the above-mentioned meanings, and $R^b$ has the meaning of $R^a$,
or
K stands for a complexing agent or complex of general formula XII

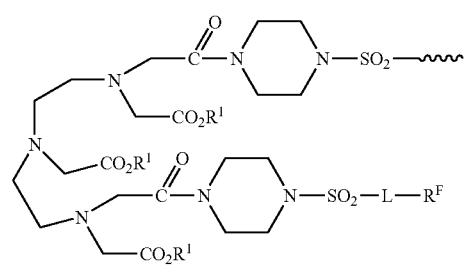

(XII)

in which L, $R^F$ and $Z^1$ have the above-mentioned meanings,
or
K stands for a complexing agent or complex of general formula XIII

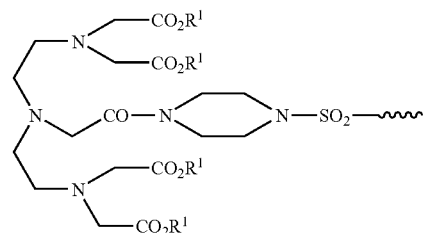

(XIII)

in which $R^1$ has the above-mentioned meaning.

9. A method according to claim 8, wherein in the compounds of general formula I, L stands for one of the following

α-$CH_2$-β

α-$CH_2CH_2$-β

α-$(CH_2)_s$-β s=3-15

α-$CH_2$—O—$CH_2CH_2$-β

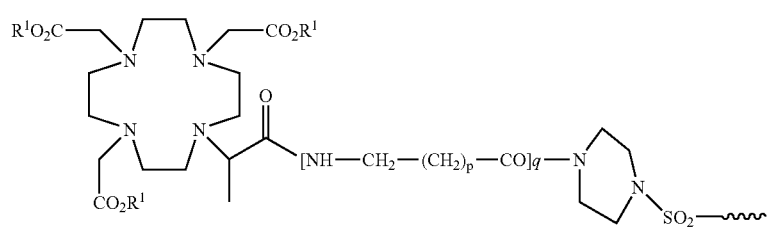

(XI)

α-CH$_2$—(O—CH$_2$—CH$_2$-)$_t$-β  t=2-6

α-CH$_2$—NH—CO-β

α-CH$_2$—NH—CO—CH$_2$—N(CH$_2$COOH)—SO$_2$-β

α-CH$_2$—NH—CO—CH$_2$—N(C$_2$H$_5$)—SO$_2$-β

α-CH$_2$—NH—CO—CH$_2$—N(C$_{10}$H$_{21}$)—SO$_2$-β

α-CH$_2$—NH—CO—CH$_2$—N(C$_6$H$_{13}$)—SO$_2$-β

α-CH$_2$—NH—CO—(CH$_2$)$_{10}$—N(C$_2$H$_5$)—SO$_2$-β

α-CH$_2$—NH—CO—CH$_2$—N(—CH$_2$—C$_6$H$_5$)—SO$_2$-β

α-CH$_2$—NH—CO—CH$_2$—N(—CH$_2$—CH$_2$—OH)SO$_2$-β

α-CH$_2$—NHCO—(CH$_2$)$_{10}$—S—CH$_2$CH$_2$-β

α-CH$_2$NHCOCH$_2$—O—CH$_2$CH$_2$-β

α-CH$_2$NHCO(CH$_2$)$_{10}$—O—CH$_2$CH$_2$-β

α-CH$_2$—C$_6$H$_4$—O—CH$_2$CH$_2$-β

α-CH$_2$—O—CH$_2$—C(CH$_2$—OCH$_2$CH$_2$—C$_6$F$_{13}$)$_2$—CH$_2$—OCH$_2$—CH$_2$-β

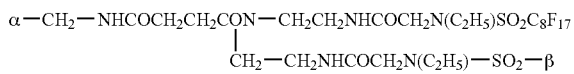

α-CH$_2$—O—CH$_2$—CH(OC$_{10}$H$_{21}$)—CH$_2$—O—CH$_2$CH$_2$-β

α-(CH$_2$NHCO)$_4$—CH$_2$O—CH$_2$CH$_2$-β

α-(CH$_2$NHCO)$_3$—CH$_2$O—CH$_2$CH$_2$-β

α-CH$_2$—OCH$_2$C(CH$_2$OH)$_2$—CH$_2$—O—CH$_2$CH$_2$-β

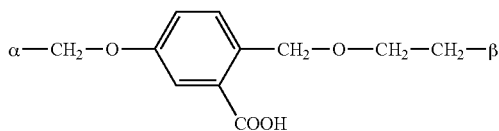

α-CH$_2$NHCOCH$_2$N(C$_6$H$_5$)—SO$_2$-β

α-NHCO—CH$_2$—CH$_2$-β

α-NHCO—CH$_2$—O—CH$_2$CH$_2$-β

α-NH—CO-β

α-NH—CO—CH$_2$—N(CH$_2$COOH)—SO$_2$-β

α-NH—CO—CH$_2$—N(C$_2$H$_5$)—SO$_2$-β

α-NH—CO—CH$_2$—N(C$_{10}$H$_{21}$)—SO$_2$-β

α-NH—CO—CH$_2$—N(C$_6$H$_{13}$)—SO$_2$-β

α-NH—CO—(CH$_2$)$_{10}$—N(C$_2$H$_5$)—SO$_2$-β

α-NH—CO—CH$_2$—N(—CH$_2$—C$_6$H$_5$)—SO$_2$-β

α-NH—CO—CH$_2$—N(—CH$_2$—CH$_2$—OH)SO$_2$-β

α-NH—CO—CH$_2$-β

α-CH$_2$—O—C$_6$H$_4$—O—CH$_2$—CH$_2$-β

α-CH$_2$—C$_6$H$_4$—O—CH$_2$—CH$_2$-β

α-N(C$_2$H$_5$)—SO$_2$-β

α-N(C$_6$H$_5$)—SO$_2$-β

α-N(C$_{10}$H$_{21}$)—SO$_2$-β

α-N(C$_6$H$_{13}$)—SO$_2$-β

α-N(C$_2$H$_4$OH)—SO$_2$-β

α-N(CH$_2$COOH)—SO$_2$-β

α-N(CH$_2$C$_6$H$_5$)—SO$_2$-β

α-N—[CH(CH$_2$OH)$_2$]—SO$_2$-β

α-N—[CH(CH$_2$OH)CH(CH$_2$OH)]—SO$_2$-β or in which α represents the binding site to the complexing agent or metal complex K, and β represents the binding site to the fluorine radical.

10. A method according to claim 8, wherein in the compounds of formula I, n in formula —C$_n$F$_{2n}$E stands for numbers 4-15 and/or E in this formula means a fluorine atom.

11. A method according to claim 8, wherein one of the following complexes are administered Gadolinium complex of 10-[1-methyl-2-oxo-3-aza-5-oxo-{4-perfluorooctylsulfonyl-piperazin-1-yl}-pentyl]-1,4,7-tris(carboxymethyl)-1,4,7,10-tetraazacyclododecane, Gadolinium complex of 10-[2-hydroxy-4-aza-5-oxo-7-oxa-10,10,11,11,12,12,13,13,14,14,15,15,16,16,17,17-heptadecafluoroheptadecyl]-1,4,7-tris(carboxymethyl)-1,4,7,10-tetraazacyclododecane, Gadolinium complex of 10-[2-hydroxy-4-aza-5,9-dioxo-9-{4-perfluorooctyl)-piperazin-1-yl}-nonyl]-1,4,7-tris(carboxymethyl)-1,4,7,10-tetraazacyclododecane, Gadolinium complex of 10-[2-hydroxy-4-aza-5-oxo-7-aza-7-(perfluorooctyl-sulfonyl)-nonyl]-1,4,7-tris(carboxymethyl)-1,4,7,10-tetraazacyclododecane, Gadolinium complex of 10-[2-hydroxy-4-oxa-1H,1H,2H,3H,3H,5H,5H,6H,6H-perfluorotetradecyl]-1,4,7-tris(carboxymethyl)-1,4,7,10-tetraazacyclododecane, Gadolinium complex of 10-[2-hydroxy-4-aza-5-oxo-7-oxa-10,10,11,11,12,12,13,13,14,14,15,15,16,16,17,17,18,18,19,19-henicosafluoro-nonadecyl]-1,4,7-tris(carboxymethyl)-1,4,7,10-tetraazacyclododecane, Gadolinium complex of 10-[2-hydroxy-4-aza-5-oxo-11-aza-11-(perfluorooctylsulfonyl)-tridecyl]-1,4,7-tris(carboxymethyl)-1,4,7,10-tetraazacyclododecane, or Gadolinium complex of 10-[2-hydroxy-4-aza-5-oxo-7-aza-7-(perfluorooctylsulfonyl)-8-phenyl-octyl]-1-4-7-tris(carboxymethyl)-1,4,7,10-tetraaza-cyclododecane.

12. A method according to claim 1, wherein the perfluoroalkyl-containing metal complexes are of formula Ia A-R$^F$    (Ia)

in which

A is a molecule part that contains 2 to 6 metal complexes, which are bonded directly or via a linker to a nitrogen atom of an annular skeleton chain, and $R^F$ is a perfluorinated, straight-chain or branched carbon chain with formula —$C_nF_{2n}E$, in which E represents a terminal fluorine, chlorine, bromine, iodine or hydrogen atom, and n stands for numbers 4-30, wherein molecule part A has the following structure:

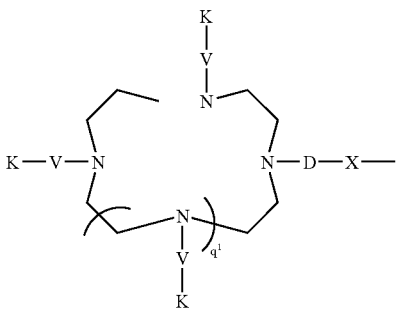

wherein $q^1$ is a number 0, 1, 2 or 3,

K stands for a complexing agent or metal complex or a salt thereof with an organic and/or inorganic base or amino acid or amino acid amide, X is a direct bond to the perfluoroalkyl group, a phenylene group or a $C_1$-$C_{10}$-alkylene chain, which optionally contains 1-15 oxygen atoms, 1-5 sulfur atoms, 1-10 carbonyl groups, 10-10 ($NR^d$) groups, 1-2 $NR^dSO_2$ groups, 1-10 $CONR^d$ groups, 1 piperidine group, 1-3 $SO_2$ groups and 1-2 phenylene groups or optionally is substituted by 1-3 radicals $R^F$, in which $R^d$ stands for a hydrogen atom, a phenyl group, benzyl group or a $C_1$-$C_{15}$ alkyl group, which optionally contains 1-2 NHCO groups, 1-2 CO groups, or 1-5 oxygen atoms and optionally is substituted by 1-5 hydroxy, 1-5 methoxy, 1-3 carboxy, or 1-3 $R^F$ radicals, V is a direct bond or a chain of general formula IIa or IIIa:

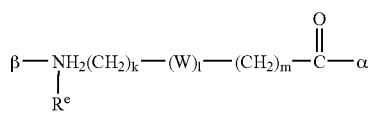

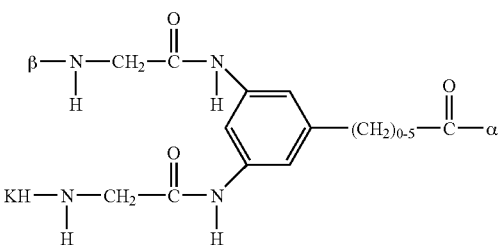

in which $R^e$ is a hydrogen atom, a phenyl group, a benzyl group or a $C_1$-$C_7$-alkyl group, which optionally is substituted with a carboxy group, a methoxy group or a hydroxy group, W is a direct bond, a polyglycol ether group with up to 5 glycol units, or a molecule part of general formula IVa $$—CH(R^h)— \quad (IVa)$$

in which $R^h$ is a $C_1$-$C_7$ carboxylic acid, a phenyl group, a benzyl group or a —$(CH_2)_{1-5}$—NH—K group, α represents the binding to the nitrogen atom of the skeleton chain, β represents the binding to complexing agents or metal complex K, and in which variables k and m stand for natural numbers between 0 and 10, and l stands for 0 or 1 and wherein D is a CO or $SO_2$ group.

13. A method according to claim 12, wherein in the compounds of general formula Ia, q is the number 1.

14. A method according to claim 12, wherein in the compounds of general formula Ia, molecule part X is an alkylene chain, which contains 1-10 $CH_2CH_2O$ groups or 1-5 $COCH_2NH$ groups, a direct bond or one of the following structures

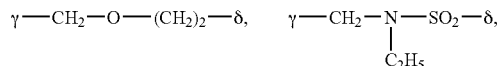
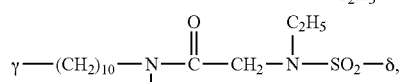
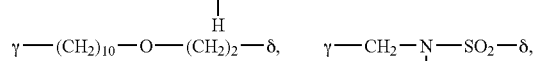
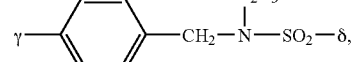
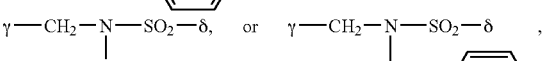

wherein

γ binds to D, and δ binds to $R^F$.

15. A method according to claim 12, wherein in the compounds of general formula Ia, V is a molecule part with one of the following structures

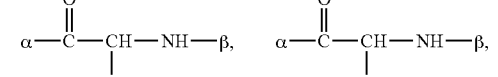
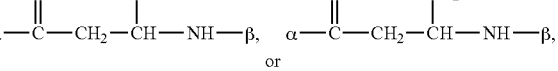

or

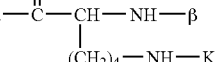
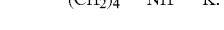

16. A method according to claim 12, wherein in the compounds of general formula Ia, K represents a complex of general formula Va, VIa, VIIa or VIIIa,

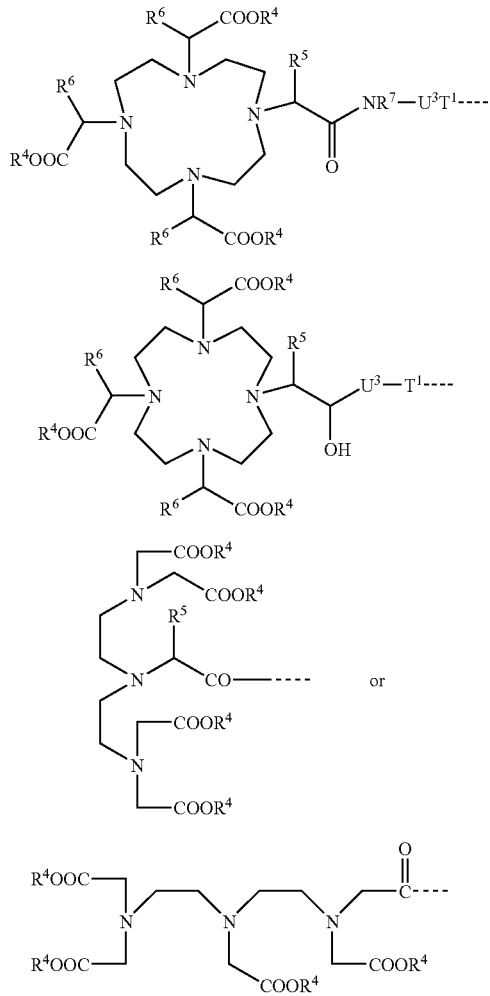

wherein
- $R^4$, independently of one another, are a hydrogen atom or a metal ion equivalent of the elements of atomic numbers 23-29, 42-46 or 58-70,
- $R^5$ is a hydrogen atom or a straight-chain, branched, saturated or unsaturated $C_1$-$C_{30}$ alkyl chain, which optionally is substituted by 1-5 hydroxy, 1-3 carboxy or 1 phenyl group(s) and/or optionally is interrupted by 1-10 oxygen atoms, 1 phenylene group or 1 phenylenoxy group,
- $R^6$ is a hydrogen atom, a straight-chain or branched $C_1$-$C_7$ alkyl radical, a phenyl radical or benzyl radical,
- $R^7$ is a hydrogen atom, a methyl group or ethyl group, which optionally is substituted by a hydroxy group or carboxy group,
- $U^3$ is a straight-chain, branched, saturated or unsaturated $C_1$-$C_{20}$ alkylene group optionally containing 1-5 imino groups, 1-3 phenylene groups, 1-3 phenylenoxy groups, 1-3 phenylenimino groups, 1-3 amide groups, 1-2 hydrazide groups, 1-5 carbonyl groups, 1-5 ethylenoxy groups, 1 urea group, 1 thiourea group, 1-2 carboxyalkylimino groups, 1-2 ester groups, 1-1-0 oxygen atoms, 1-5 sulfur atoms and/or 1-5 nitrogen atoms, and/or optionally substituted by 1-5 hydroxy groups, 1-2 mercapto groups, 1-5 oxo groups, 1-5 thioxo groups, 1-3 carboxy groups, 1-5 carboxyalkyl groups, 1-5 ester groups and/or 1-3 amino groups, wherein the optionally contained phenylene groups can be substituted by 1-2 carboxy groups, 1-2 sulfone groups or 1-2 hydroxy groups
- $T^1$ stands for a —CO-β, —NHCO-β or —NHCS-β group, wherein β represents the binding site to V.

17. A method according to claim 16, wherein the $C_1$-$C_{20}$-alkylene chain that stands for $U^3$ contains the groups —$CH_2NHCO$—, —$NHCOCH_2O$—, —$NHCOCH_2OC_6H_4$—, —$N(CH_2CO_2H)$—, —$CH_2OCH_2$—, —$NHCOCH_2C_6H_4$—, —$NHCSNHC_6H_4$—, —$CH_2OC_6H_4$—, or —$CH_2CH_2O$— and/or is substituted by the groups —COOH or —$CH_2COOH$.

18. A method according to claim 16, wherein $U^3$ stands for a —$CH_2$—, —$CH_2CH_2$—, —$CH_2CH_2CH_2$—, —$C_6H_4$—, —$C_6H_{10}$—, —$CH_2C_6H_4$—, —$CH_2NHCOCH_2CH(CH_2CO_2H)$—$C_6H_4$—, —$CH_2NHCOCH_2OCH_2$—, or —$CH_2NHCOCH_2C_6H_4$— group.

19. A method according to claim 12, wherein in the compounds of general formula Ia, K has one of the following structures:

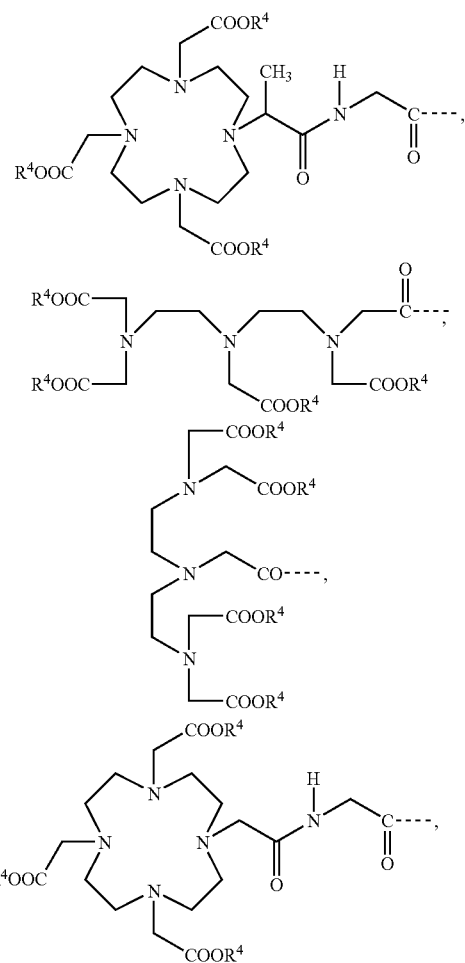

-continued

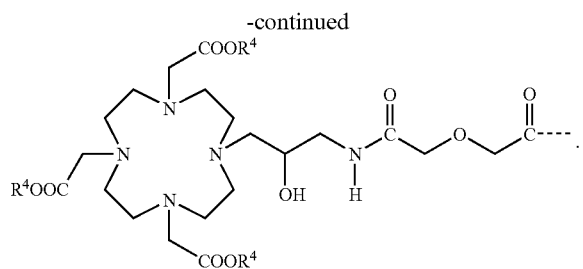

20. A method according to claim 12, wherein in the compounds of general formula Ia, the perfluoroalkyl chain $R^F$ is $-C_6F_{13}$, $-C_8F_{17}$, $-C_{10}F_{21}$ or $-C_{12}F_{25}$.

21. A method according to claim 12, wherein the gadolinium complex of 1,4,7-tris{1,4,7-tris(N-(carboxylatomethyl)-10-[N-1-methyl-3,6-diaza-2,5,8-trioxooctane-1,8-diyl)]-1,4,7,10-tetraazacyclododecane or Gd complex}-10-[N-2H,2H,4H,4H,5H,5H-3-oxa-perfluorotridecanoyl]-1,4,7,10-tetraazacyclododecane is administered.

22. A method according to claim 1, wherein the perfluoroalkyl-containing metal complexes are of formula Ib

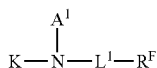

(Ib)

in which

K means a complexing agent or a metal complex of general formula IIb

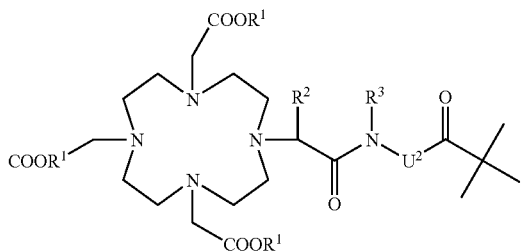

(IIb)

wherein

R$^1$ stands for a hydrogen atom or a metal ion equivalent of atomic numbers 23-29, 42-46 or 58-70, R$^2$ and R$^3$ stand for a hydrogen atom, a C$_1$-C$_7$-alkyl group, a benzyl group, a phenyl group, —CH$_2$OH or —CH$_2$—OCH$_3$, U$^2$ stands for radical L$^1$, wherein L$^1$ and U$^2$, independently of one another, can be the same or different, however, A$^1$ means a hydrogen atom, a straight-chain or branched C$_1$-C$_{30}$ alkyl group, which optionally is interrupted by 1-15 oxygen atoms, and/or optionally is substituted with 1-10 hydroxy groups, 1-2 COOH groups, a phenyl group, a benzyl group and/or 1-5 —OR$^9$ groups, with R$^9$ in the meaning of a hydrogen atom or a C$_1$-C$_7$ alkyl radical, or -L$^1$-R$^F$, L$^1$ means a straight-chain or branched C$_1$-C$_{30}$-alkylene group, which optionally is interrupted by 1-10 oxygen atoms, 1-5 —NH—CO groups, 1-5 —CO—NH groups, by a phenylene group optionally substituted by a COOH— group, 1-3 sulfur atoms, 1-2 —N(B$^1$)—SO$_2$ groups and/or 1-2 —SO$_2$—N(B$^1$)-groups with B$^1$ in the meaning of A$^1$, and/or optionally is substituted with radical R$^F$, and R$^F$ means a straight-chain or branched perfluorinated alkyl radical of formula C$_n$F$_{2n}$E, wherein n stands for numbers 4-30, and E stands for a terminal fluorine atom, chlorine atom, bromine atom, iodine atom or a hydrogen atom, and optionally present acid groups optionally can be present as salts of organic and/or inorganic bases or amino acids or amino acid amides.

23. A method according to claim 22, wherein in the compounds of general formula Ib, R$^2$, R$^3$ and R$^9$, independently of one another, mean hydrogen or a C$_1$-C$_4$ alkyl group.

24. A method according to claim 22, wherein in the compounds of general formula Ib, A$^1$ means hydrogen, a C$_1$-C$_{15}$ alkyl radical, or one of the radicals $C_2H_4-O-CH_3$, $C_3H_6-O-CH_3$, $C_2H_4-O-(C_2H_4-O)_t-C_2H_4-OH$, $C_2H_4-O-(C_2H_4-O)_t-C_2H_4-OCH_3$, $C_2H_4OH$, $C_3H_6OH$, $C_4H_8OH$, $C_5H_{10}OH$, $C_6H_{12}OH$, $C_7H_{14}OH$, $CH(OH)CH_2OH$, $CH(OH)CH(OH)CH_2OH$, $CH_2[CH(OH)]_{u^1}CH_2OH$, $CH[CH_2(OH)]CH(OH)CH_2OH$, $C_2H_4CH(OH)CH_2OH$, $(CH_2)_sCOOH$, $C_2H_4-O-(C_2H_4-O)_t-CH_2COOH$ or $C_2H_4-O-(C_2H_4-O)_t-C_2H_4-C_nF_{2n}E$ wherein s stands for integers 1 to 15, t stands for integers 0 to 13, u$^1$ stands for integers 1 to 10, n stands for integers 4 to 20, and E stands for hydrogen, fluorine, chlorine, bromine or iodine atoms, or a branched isomer thereof.

25. A method according to claim 22, wherein in the compounds of general formula Ib, A$^1$ means hydrogen, C$_1$-C$_{10}$ alkyl, or one of the following $C_2H_4-O-CH_3$, $C_3H_6-O-CH_3$, $C_2H_4-O-(C_2H_4-O)_x-C_2H_4-OH$, $C_2H_4-O-(C_2H_4-O)_x-C_2H_4-OCH_3$, $C_2H_4OH$, $C_3H_6OH$, $CH_2[CH(OH)]_yCH_2OH$, $CH[CH_2(OH)]CH(OH)CH_2OH$, $(CH_2)_wCOOH$, $C_2H_4-O-(C_2H_4-O)_x-CH_2COOH$, or $C_2H_4-O-(C_2H_4-O)_x-C_2H_4-C_nF_{2n}E$, wherein
x stands for integers 0 to 5,
y stands for integers 1 to 6,
w stands for integers 1 to 10,
n stands for integers 4 to 15, and
E stands for a fluorine atom,
or a branched isomer thereof.

26. A method according to claim 22, wherein in the compounds of general formula Ib, L1 means one of the following α-$(CH_2)_s$-β

α-$CH_2-CH_2-(O-CH_2-CH_2-)_y$-β

α-$CH_2-(O-CH_2-CH_2-)_y$-β

α-$CH_2-NH-CO$-β

α-$CH_2-CH_2-NH-SO_2$-β

α-$CH_2-NH-CO-CH_2-N(CH_2COOH)-SO_2$-β

α-$CH_2-NH-CO-CH_2-N(C_2H_5)-SO_2$-β

α-$CH_2-NH-CO-CH_2-N(C_{10}H_{21})-SO_2$-β

α-$CH_2-NH-CO-CH_2-N(C_6H_{13})-SO_2$-β

α-$CH_2-NH-CO-(CH_2)_{10}-N(C_2H_5)-SO_2$-β

α-$CH_2-NH-CO-CH_2-N(-CH_2-C_6H_5)-SO_2$-β

α-$CH_2-NH-CO-CH_2-N(-CH_2-CH_2-OH)SO_2$-β

α-$CH_2-NHCO-(CH_2)_{10}-S-CH_2CH_2$-β

α-$CH_2NHCOCH_2-O-CH_2CH_2$-β

α-$CH_2-CH_2NHCOCH_2-O-CH_2CH_2$-β

α-$CH_2-(CH_2-CH_2-O)_t-(CH_2)_3NHCO-CH_2-O-CH_2CH_2$-β

α-$CH_2NHCO(CH_2)_{10}-O-CH_2CH_2$-β

α-$CH_2CH_2NHCO(CH_2)_{10}-O-CH_2CH_2$-β

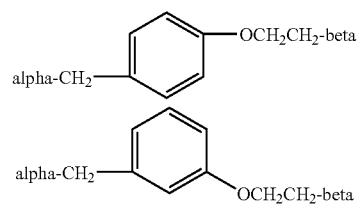

α-$CH_2-O-CH_2-C(CH_2-OCH_2-CH_2-C_6F_{13})_2-CH_2-OCH_2-CH_2$-β

α-$CH_2-NHCOCH_2CH_2CON-CH_2CH_2NHCOCH_2N(C_2H_5)SO_2C_8F_{17}$-β

α-$CH_2-CH_2NHCOCH_2N(C_2H_5)-SO_2$-β

α-$CH_2-O-CH_2-CH(OC_{10}H_{21})-CH_2-O-CH_2CH_2$-β

α-$(CH_2-NHCO)_4-CH_2O-CH_2CH_2$-β

α-$(CH_2-NHCO)_3-CH_2O-CH_2CH_2$-β

α-$CH_2-OCH_2C(CH_2OH)_2-CH_2-O-CH_2CH_2$-β

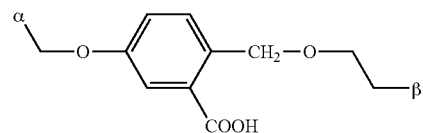

α-$CH_2NHCOCH_2N(C_6H_5)-SO_2$-β

α-$NHCO-CH_2-CH_2$-β

α-$NHCO-CH_2-O-CH_2CH_2$-β

α-$NH-CO$-β

α-$NH-CO-CH_2-N(CH_2COOH)-SO_2$-β

α-$NH-CO-CH_2-N(C_2H_5)-SO_2$-β

α-$NH-CO-CH_2-N(C_{10}H_{21})-SO_2$-β

α-$NH-CO-CH_2-N(C_6H_{13})-SO_2$-β

α-$NH-CO-(CH_2)_{10}-N(C_2H_5)-SO_2$-β

α-$NH-CO-CH_2-N(-CH_2-C_6H_5)-SO_2$-β

α-$NH-CO-CH_2-N(-CH_2-CH_2-OH)SO_2$-β

α-$NH-CO-CH_2$-β

α-$CH_2-O-C_6H_4-O-CH_2-CH_2$-β

α-$CH_2-C_6H_4-O-CH_2-CH_2$-β

α-$N(C_2H_5)-SO_2$-β

α-$N(C_6H_5)-SO_2$-β

α-$N(C_{10}H_{21})-SO_2$-β

α-$N(C_6H_{13})-SO_2$-β

α-$N(C_2H_4OH)-SO_2$-β

α-$N(CH_2COOH)-SO_2$-β

α-$N(CH_2C_6H_5)-SO_2$-β

α-$N-[CH(CH_2OH)_2]-SO_2$-β or

α-$N-[CH(CH_2OH)CH(CH_2OH)]-SO_2$-β wherein
s stands for integers 1 to 15 and
y stands for integers 1 to 6.

27. A method according to claim 22, wherein in the compounds of general formula Ib, $L^1$ means one of the following

α-CH₂—O—CH₂CH₂-β,

α-CH₂—CH₂—(O—CH₂—CH₂—)ᵧ-β,

α-CH₂—(O—CH₂—CH₂—)ᵧ-β,

α-CH₂—CH₂—NH—SO₂-β,

α-CH₂NCHOCH₂—O—CH₂CH₂-β,

α-CH₂—CH₂NHCOCH₂—O—CH₂CH₂-β,

α-CH₂—(CH₂—CH₂—O)ᵧ—(CH₂)₃NHCO—CH₉—O—CH₂CH₂-β,

α-CH₂NHCO(CH₂)₁₀—O—CH₂CH₂-β,

α-CH₂CH₂NHCO(CH₂)₁₀—O—CH₂CH₂-β,

α-CH₂—O—CH₂—CH(OC₁₀OH₂₁)—CH₂—O—CH₂CH₂β,

α-CH₂—O—C₆H₄—O—CH₂—CH₂-β or

α-CH₂—C₆H₄—O—CH₂—CH₂-β wherein y stands for integers 1 to 6.

28. A method according to claim 22, wherein in the compounds of general formula Ib, $R^F$ means a straight-chain or branched perfluorinated alkyl radical of formula $C_nF_{2n}E$, wherein n stands for numbers 4 to 15 and E stands for a terminal fluorine atom.

29. A method according to claim 22, wherein one of the following complexes are administered:

1,4,7-Tris(carboxylatomethyl)-10-(3-aza-4-oxo-hexan-5-ylic)-acid-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex 1,4,7-Tris(carboxylatomethyl)-10-{(3-aza-4-oxo-hexan-5-ylic)acid-N-(3,6,9,12,15-pentaoxa)-hexadecyl)-(1H,1H,2H,2H,4H,4H,5H,5H-3-oxa)-perfluorotridecyl]-amide}-1,4,7,10-tetraazacyclododecane, gadolinium complex 1,4,7-Tris(carboxylatomethyl)-10-{(3-aza-4-oxo-hexan-5-ylic)-acid-N-5-hydroxy-3-oxa-pentyl)-N-(1H,1H,2H,2H,4H,4H,5H,5H-3-oxa)-perfluorotridecyl]-amide}-1,4,7,10-tetraazacyclododecane, gadolinium complex 1,4,7-Tris(carboxylatomethyl)-10-{(3-aza-4-oxo-hexan-5-ylic)-acid-[N-3,6,9,15-tetraoxa-12-aza-15-oxo-C₁₇-C₂₆-hepta-decafluoro)hexacosyl]-amide}-1,4,7,10-tetraazacyclododecane, gadolinium complex 1,4,7-Tris(carboxylatomethyl)-10-[(3-aza-4-oxo-hexan-5-ylic]-acid-N-(2-methoxyethyl)-N-(1H,1H,2H,2H,4H,4H,5H,5H-3-oxa)-perfluorotridecyl]-amide}-1,4,7,10-tetraazacyclododecane, gadolinium complex.

30. A method according to claim 1, wherein the perfluoroalkyl-containing metal complexes are of formula Ic

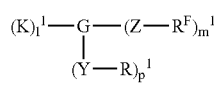

(Ic)

in which

R represents a mono- or oligosaccharide radical bonded by the 1-OH— or 1-SH— position, $R^F$ is a perfluorinated, straight-chain or branched carbon chain with the formula $—C_nF_{2n}E$, in which E represents a terminal fluorine, chlorine, bromine, iodine or hydrogen atom, and n stands for numbers 4-30, K stands for a metal complex of general formula IIe,

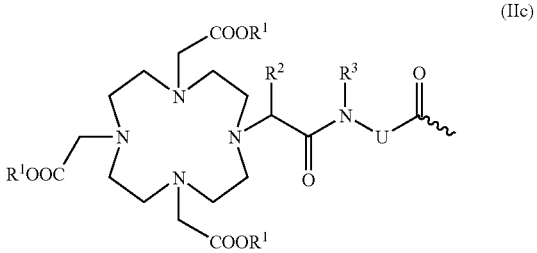

(IIc)

in which $R^1$ means a hydrogen atom or a metal ion equivalent of atomic numbers 23-29, 42-46 or 58-70, provided that at least two $R^1$ stand for metal ion equivalents, $R^2$ and $R^3$, independently of one another, represent hydrogen, $C_1$-$C_7$-alkyl, benzyl, phenyl, —CH₂OH or —CH₂OCH₃, and U represents —C₆H₄—O—CH₂-ω, —(CH₂)₁₋₅-ω, a phenylene group, —CH₂—NHCO—CH₂—CH(CH₂COOH)—C₆H₄-ω, —C₆H₄—(OCH₂CH₂)₀₋₁—N(CH₂COOH)—CH₂-ω, or a $C_1$-$C_{12}$-alkylene group or $C_7$—$C_{12}$—$C_6H_4$—O group optionally interrupted by one or more oxygen atoms, 1 to 3 —NHCO groups or 1 to 3 —CONH groups and/or substituted with 1 to 3 —(CH₂)₀₋₅ COOH groups, wherein m stands for the binding site to —CO—, or of general formula IIIc

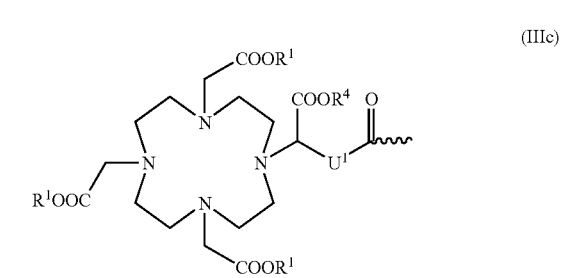

(IIIc)

in which $R^1$ has the above-mentioned meaning, $R^4$ represents hydrogen or a metal ion equivalent mentioned under $R^1$, and $U^1$ represents —C₆H₄—O—CH₂-ω, wherein ω means the binding site to —CO—, or of general formula IVc

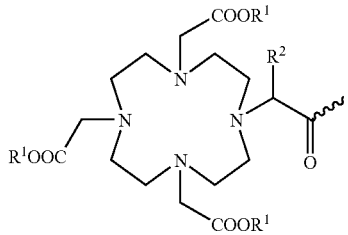
(IVc)

in which $R^1$ and $R^2$ have the above-mentioned meaning
or of general formula VcA or VcB

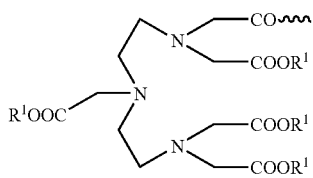
(VcA)

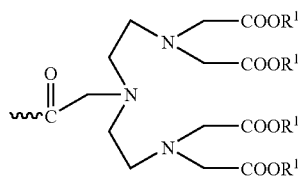
(VcB)

in which $R^1$ has the above-mentioned meaning,
or of general formula VIc

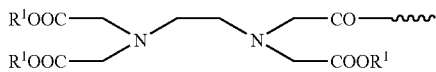
(VIc)

in which $R^1$ has the above-mentioned meaning,
or of general formula VIIc

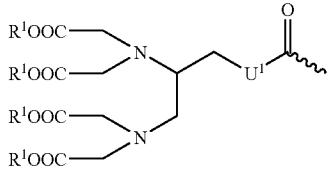
(VIIc)

in which $R^1$ has the above-mentioned meaning, and
$U^1$ represents —$C_6H_4$—O—$CH_2$-ω, wherein ω means the binding site to —CO—
or of general formula VIIIc

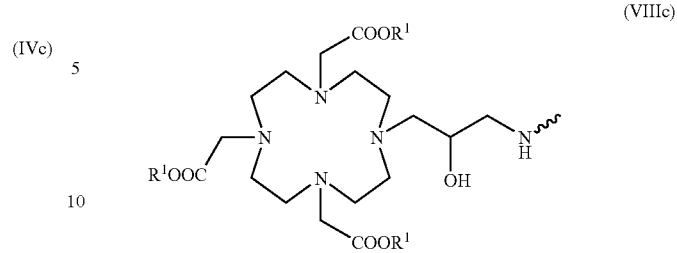
(VIIIc)

in which $R^1$ has the above-mentioned meaning, and in radical K, optionally present free acid groups optionally can be present as salts of organic and/or inorganic bases or amino acids or amino acid amides, G for the case that K means a metal complex of IIc to VIIc, represents a radical that is functionalized in at least three places and is selected from the following radicals a) to j)

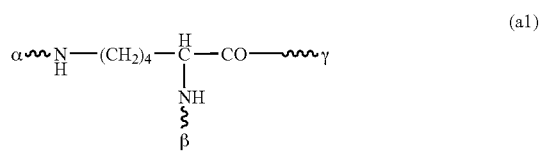
(a1)

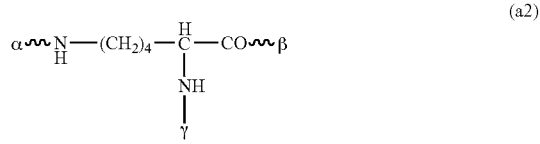
(a2)

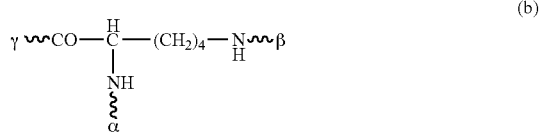
(b)

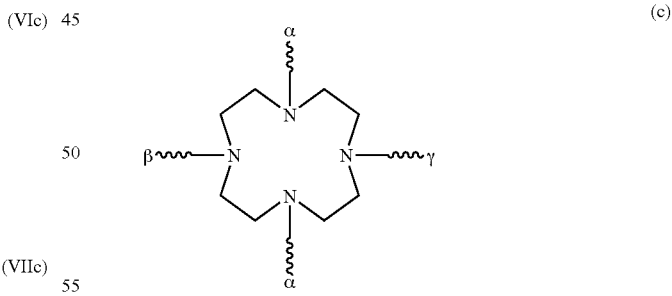
(c)

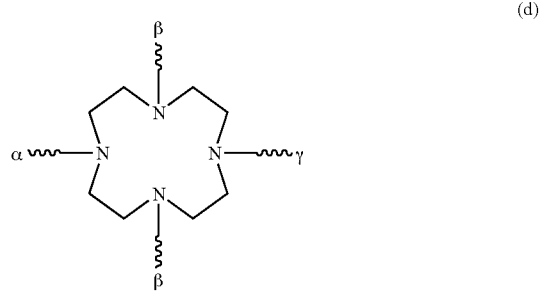
(d)

-continued

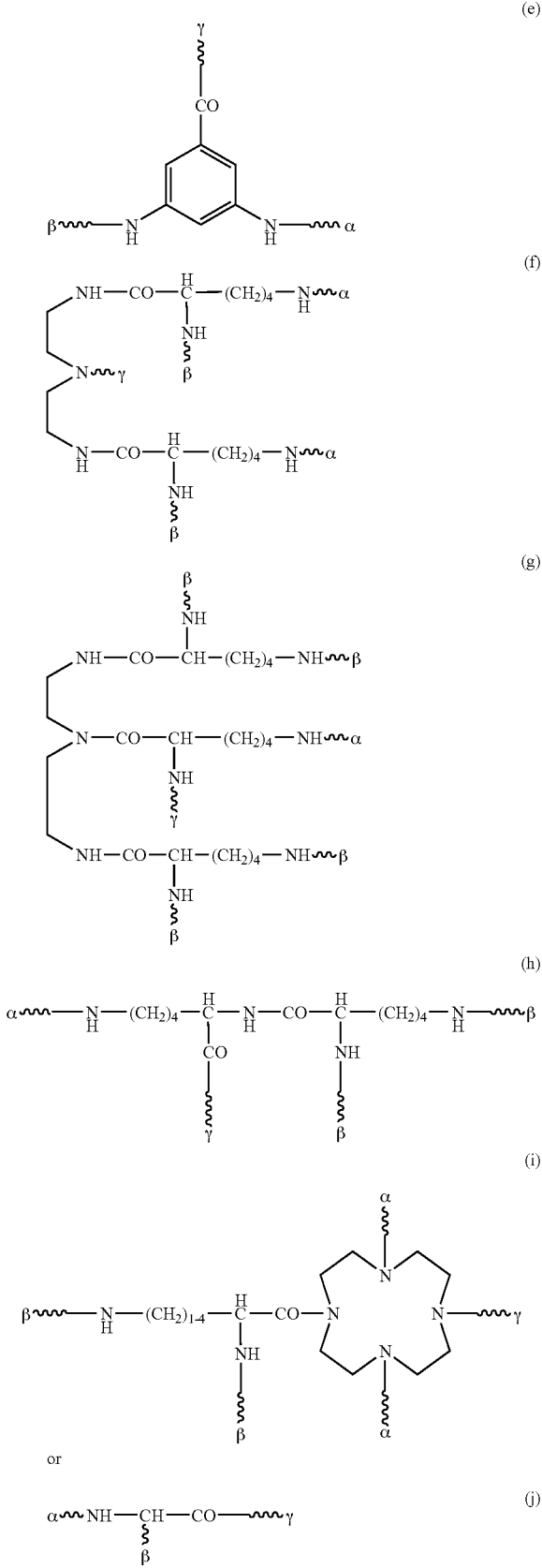

G for the case that K means a metal complex VIIIc, represents a radical that is functionalized in at least three places and is selected from k) or l),

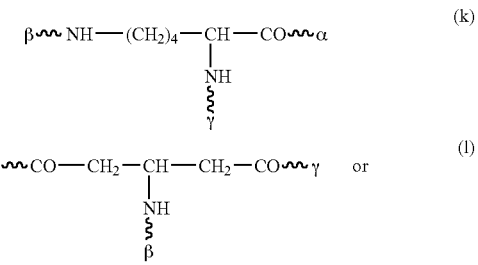

wherein α means the binding site of G to complex K, β is the binding site of G to radical Y, and γ represents the binding site of G to radical Z, Y means —$CH_2$, δ-$(CH_2)_{(1-5)}$CO-β, β-$(CH_2)_{(1-5)}$CO-δ, δ-$CH_2$—CHOH—CO-δ or δ-CH(CHOH—$CH_2$OH)—CHOH—CHOH—CO-β, wherein δ represents the binding site to sugar radical R and β is the binding site to radical G, Z stands for

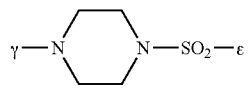

γ-$COCH_2$—N($C_2H_5$)—$SO_2$-ε,

γ-$COCH_2$—O—$(CH_2)_2$—$SO_2$-ε,

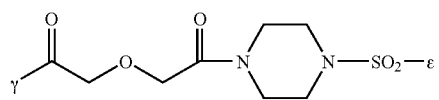

or

γ-$NHCH_2CH_2$—O—$CH_2CH_2$-ξ wherein γ represents the binding site of Z to radical G, and ξ means the binding site of Z to perfluorinated radical $R^F$ and $l^1$, $m^1$, independently of one another, mean integers 1 or 2, and $p^1$ means integers 1 to 4.

31. A method according to claim 30, wherein in the compounds of general formula Ic, R represents a monosaccharide radical with 5 to 6 C atoms or its deoxy compound or is glucose, mannose or galactose.

32. A method according to claim 30, wherein in the compounds of general formula Ic, $R^2$ and $R^3$, independently of one another, mean hydrogen or $C_1$-$C_4$ alkyl and/or E in formula —$C_nF_{2n}$E means a fluorine atom.

33. A method according to claim 30, wherein in the compounds of general formula Ic, G represents lysine radical (a) or (b).

34. A method according to claim 30, wherein in the compounds of general formula Ic, Z means

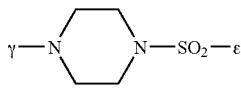

wherein γ represents the binding site of Z to radical G, and ξ means the binding site of Z to perfluorinated radical $R^F$, and/or Y means δ-$CH_2$COβ, wherein δ represents the binding site to sugar radical R and β represents the binding site to radical G.

35. A method according to claim 30, wherein in the compounds of general formula Ic, U in metal complex K represents —$CH_2$— or —$C_6H_4$—O—$CH_2$-ω, wherein ω stands for the binding site to —CO—.

36. A method according to claim 30, wherein the gadolinium complex of 6-N-[1,4,7-tris(carboxylatomethyl)-1,4,7,10-tetraazacyclododecane-10-N-(pentanoyl-3-aza-4-oxo-5-methyl-5-yl)]-2-N-[1-O-α-D-carbonylmethyl-mannopyranose]-L-lysine-[1-(4-perfluorooctylsulfonyl)-piperazine]-amide is administered.

37. A method according to claim 1, wherein the perfluoroalkyl-containing metal complexes are of formula Id

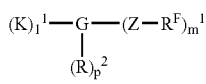
(Id)

in which
$R^F$ is a perfluorinated, straight-chain or branched carbon chain with formula —$C_nF_{2n}$E, in which E represents a terminal fluorine, chlorine, bromine, iodine or hydrogen atom, and n stands for numbers 4-30,
K stands for a metal complex of general formula IId,

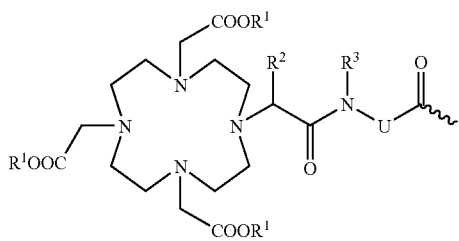
(IId)

in which
$R^1$ means a hydrogen atom or a metal ion equivalent of atomic numbers 23-29, 42-46 or 58-70,
provided that at least two $R^1$ stand for metal ion equivalents,
$R^2$ and $R^3$, independently of one another, represent hydrogen, $C_1$-$C_7$ alkyl, benzyl, phenyl, —$CH_2$OH or —$CH_2OCH_3$, and
U represents —$C_6H_4$—O—$CH_2$-ω-, —$(CH_2)_{1-5}$-ω, a phenylene group, —$CH_2$—NHCO—$CH_2$—CH($CH_2$COOH)—$C_6H_4$-ω-, —$C_6H_4$—(O$CH_2CH_2$)$_{0-1}$—N($CH_2$COOH)—$CH_2$-ω, or a $C_1$-$C_{12}$ alkylene group or $C_7$-$C_{12}$—$C_6H_4$-O group optionally interrupted by one or more oxygen atoms, 1 to 3 —NHCO groups, 1 to 3 —CONH groups and/or substituted with 1 to 3 —$(CH_2)_{0-5}$COOH groups, wherein w stands for the binding site to —CO—, or
of general formula IIId

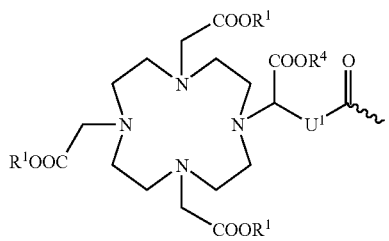
(IIId)

in which $R^1$ has the above-mentioned meaning, $R^4$ represents hydrogen or a metal ion equivalent mentioned under $R^1$, and $U^1$ represents —$C_6H_4$—O—$CH_2$-ω-, wherein ω means the binding site to —CO—, or
of general formula IVd

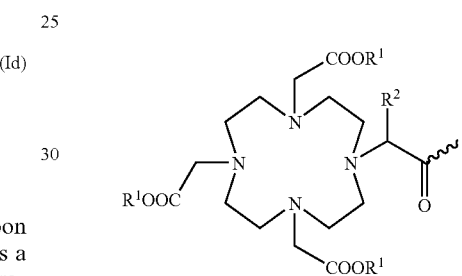
(IVd)

in which $R^1$ and $R^2$ have the above-mentioned meaning,
or of general formula VdA or VdB

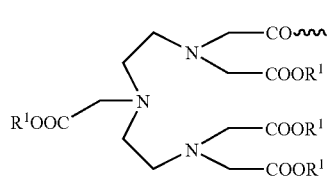
(VdA)

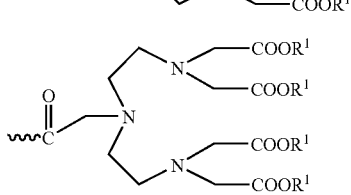
(VdB)

or in which $R^1$ has the above-mentioned meaning,
or of general formula VId

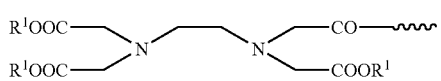
(VId)

in which $R^1$ has the above-mentioned meaning,
or of general formula VIId

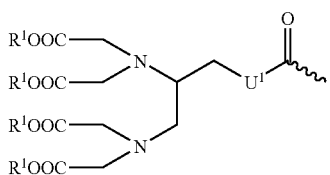
(VIId)

in which R¹ has the above-mentioned meaning, and

U¹ represents —C₆H₄—O—CH₂-ω-, wherein ω means the binding site to —CO—, and in radical K, optionally present free acid groups optionally can be present as salts of organic and/or inorganic bases or amino acids or amino acid amides, G represents a radical that is functionalized in at least three places and is selected from the following radicals a) to g)

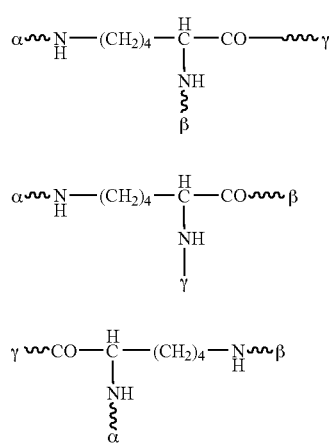

(a1)

(a2)

(b)

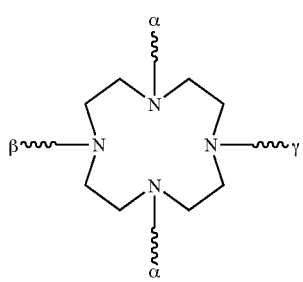

(c)

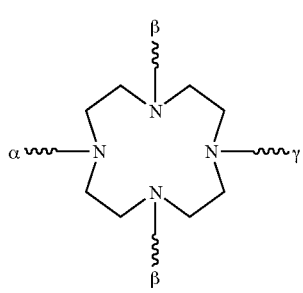

(d)

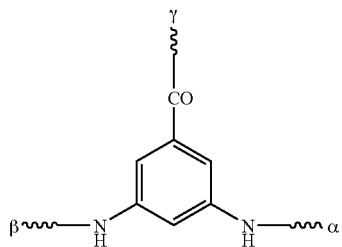

(e)

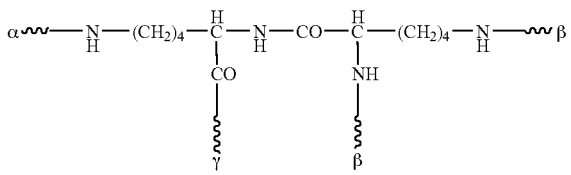

(f)

(g)

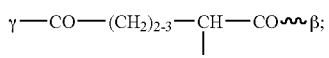

(h)

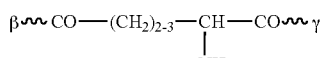

(i)

or wherein α means the binding site of G to complex K, β is the binding site of G to radical R, and γ represents the binding site of G to radical Z Z stands for

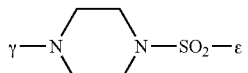

γ-C(O)CH₂O(CH₂)₂-ε, or wherein γ represents the binding site of Z to radical G and ξ means the binding site of Z to perfluorinated radical $R_f$, R represents a polar radical that is selected from complexes K of general formulas IId to VIId, wherein R¹ here means a hydrogen atom or a metal ion equivalent of atomic numbers 20, 23-29, 42-46 or 58-70, and radicals R², R³, R⁴, U and U¹ have the above-indicated meaning, or means the folic acid radical or means a carbon chain with 2-30 C atoms that is bonded to radical G via —CO— or SO$_2$— or a direct bond to radical G, and is straight or branched, saturated or unsaturated, optionally interrupted by 1-10 oxygen atoms, 1-5 —NHCO groups, 1-5 —CONH groups, 1-2 sulfur atoms, 1-5 —NH groups or 1-2 phenylene groups, which optionally can be substituted with 1-2 OH groups, 1-2 NH$_2$ groups, 1-2 —COOH groups, or 1-2 —SO$_3$H groups, or optionally substituted with 1-8 OH groups, 1-5 —COOH groups, 1-2 SO$_3$H groups, 1-5 NH$_2$ groups, or 1-5 C$_1$-C$_4$ alkoxy groups, and $l^1$, $m^1$, $p^2$, independently of one another, mean integers 1 or 2.

38. A method according to claim 37, wherein in the compounds of general formula Id, K stands for a metal complex of general formula IId, IIId, VdB or VIId.

39. A method according to claim 37, wherein in the compounds of general formula Id, polar radical R has the meaning of complex K.

40. A method according to claim 37, wherein in the compounds of general formula Id, polar radical R has one of the following meanings:

—C(O)CH$_2$CH$_2$SO$_3$H

—C(O)CH$_2$OCH$_2$CH$_2$OCH$_2$CH$_2$OH

—C(O)CH$_2$OCH$_2$CH$_2$OH

—C(O)CH$_2$OCH$_2$CH(OH)CH$_2$OH

—C(O)CH$_2$NH—C(O)CH$_2$COOH

—C(O)CH$_2$CH(OH)CH$_2$OH

—C(O)CH$_2$OCH$_2$COOH

—SO$_2$CH$_2$CH$_2$COOH

—C(O)—C$_6$H$_3$-(m-COOH)$_2$

—C(O)CH$_2$O(CH$_2$)$_2$—C$_6$H$_3$-(m-COOH)$_2$

—C(O)C H$_2$O—C$_6$H$_4$-m-SO$_3$H

—C(O)CH$_2$NHC(O)CH$_2$NHC(O)CH$_2$OCH$_2$COOH

—C(O)CH$_2$OCH$_2$CH$_2$OCH$_2$COOH

—C(O)C H$_2$OCH$_2$CH(OH)CH$_2$O—CH$_2$CH$_2$OH

—C(O)CH$_2$OCH$_2$CH(OH)CH$_2$OCH$_2$—CH(OH)—CH$_2$OH

—C(O)CH$_2$SO$_3$H

—C(O)CH$_2$CH$_2$COOH

—C(O)CH(OH)CH(OH)CH$_2$OH

—C(O)CH$_2$O[(CH$_2$)$_2$O]$_{1-9}$—CH$_3$

—C(O)CH$_2$O[(CH$_2$)$_2$O]$_{1-9}$—H

—C(O)CH$_2$OCH(CH$_2$OH)$_2$

—C(O)CH$_2$OCH(CH$_2$OCH$_2$COOH)$_2$

—C(O)—C$_6$H$_3$-(m-OCH$_2$COOH)$_2$

—CO—CH$_2$O—(CH$_2$)$_2$O(CH$_2$)$_2$O—(CH$_2$)$_2$O(CH$_2$)$_2$OCH$_3$ or

—C(O)CH$_2$O[(CH$_2$)$_2$O]$_4$—CH$_3$.

41. A method according to claim 37, wherein in the compounds of general formula Id, polar radical R is the folic acid radical.

42. A method according to claim 37, wherein in the compounds of general formula Id, G represents lysine radical (a) or (b).

43. A method according to claim 37, wherein in the compounds of general formula Id, U represents group —CH$_2$— or —C$_6$H$_4$—O—CH$_2$-ω in metal complex K, wherein ω stands for the binding site to —CO—.

44. A method according to claim 37, wherein the gadolinium complex of 2,6-N,N'-bis[1,4,7-tris(carboxylatomethyl)-1,4,7,10-tetraazacyclododecane-10-(pentanoyl-3-aza-4-oxo-5-methyl-5-yl)]-lysine-[1-(4-perfluorooctylsulfonyl-piperazine]-amide is administered.

45. A method according to claim 12, wherein the perfluoroalkyl-containing metal complexes are galenical formulations that contain paramagnetic, perfluoroalkyl-containing metal complexes of general formula Ia and diamagnetic perfluoroalkyl-containing substances, optionally dissolved in an aqueous solvent.

46. A method according to claim 45, wherein the diamagnetic perfluoroalkyl-containing substances are of formula XX $$R^F\text{-}L^2\text{-}B^2 \qquad (XX)$$

in which $R^F$ represents a straight-chain or branched perfluoroalkyl radical with 4 to 30 carbon atoms, $L^2$ stands for a linker and $B^2$ stands for a hydrophilic group.

47. A method according to claim 46, wherein linker $L^2$ is a direct bond, an —SO$_2$ group, or a straight-chain or branched carbon chain with up to 20 carbon atoms, which can be substituted with one or more —OH, —COO—, or —SO$_3$ groups and/or optionally contains one or more —O—, —S—, —CO—, —CONH—, —NHCO—, —CONR$^9$—, —NR$^9$CO—, —SO$_2$—, —PO$_4^-$—, —NH— or —NR$^9$ groups, an aryl ring or a piperazine, whereby R$^9$ stands for a C$_1$-to C$_{20}$-alkyl radical, which in turn can contain one or more O atoms, and/or can be substituted with —COO$^-$ or SO$_3$ groups.

48. A method according to claim 46, wherein hydrophilic group B$^2$ is a mono- or disaccharide, one or more adjacent —COO$^-$ or —SO$_3$ groups, a dicarboxylic acid, an isophthalic acid, a picolinic acid, a benzenesulfonic acid, a tetrahydropyrandicarboxylic acid, a 2,6-pyridinedicarboxylic acid, a quaternary ammonium ion, an aminopolycarboxylic acid, an aminodipolyethylene glycolsulfonic acid, an aminopolyethylene glycol group, an SO$_2$—(CH$_2$)$_2$—OH group, a polyhydroxyalkyl chain with at least two hydroxyl groups or one or more polyethylene glycol chains with at least two glycol units, whereby the polyethylene glycol chains are terminated by an —OH or —OCH$_3$ group.

49. A method according to claim 45, wherein the diamagnetic perfluoroalkyl-containing substances, conjugates that consist of α-, β- or γ-cyclodextrin and compounds of general formula XXII $$A^1\text{-}L^3\text{-}R^F \qquad (XXII)$$

in which A$^2$ stands for an adamantane, biphenyl or anthracene molecule, L$^3$ stands for a linker, and R$^F$ stands for a straight-chain or branched perfluoroalkyl radical with 4 to 30 carbon atoms, and whereby linker $L^3$ is a straight-chain hydrocarbon chain with 1 to 20 carbon atoms, which can be interrupted by one or more oxygen atoms, one or more CO—, $SO_2$—, CONH—, NHCO—, $CONR^{10}$—, $NR^{10}CO$—, NH— or $NR^{10}$ groups or a piperazine, whereby $R^{10}$ is a $C_1$-$C_5$ alkyl radical.

50. A method according to claim 45, wherein the diamagnetic perfluoroalkyl-containing substances, those of general formula XXI:

$$R^F\text{—}X^1 \quad (XXI)$$

in which $R^F$ represents a straight-chain or branched perfluoroalkyl radical with 4 to 30 carbon atoms, and $X^1$ is a radical that is selected from the group of the following radicals, wherein n is a number between 1 and 10:

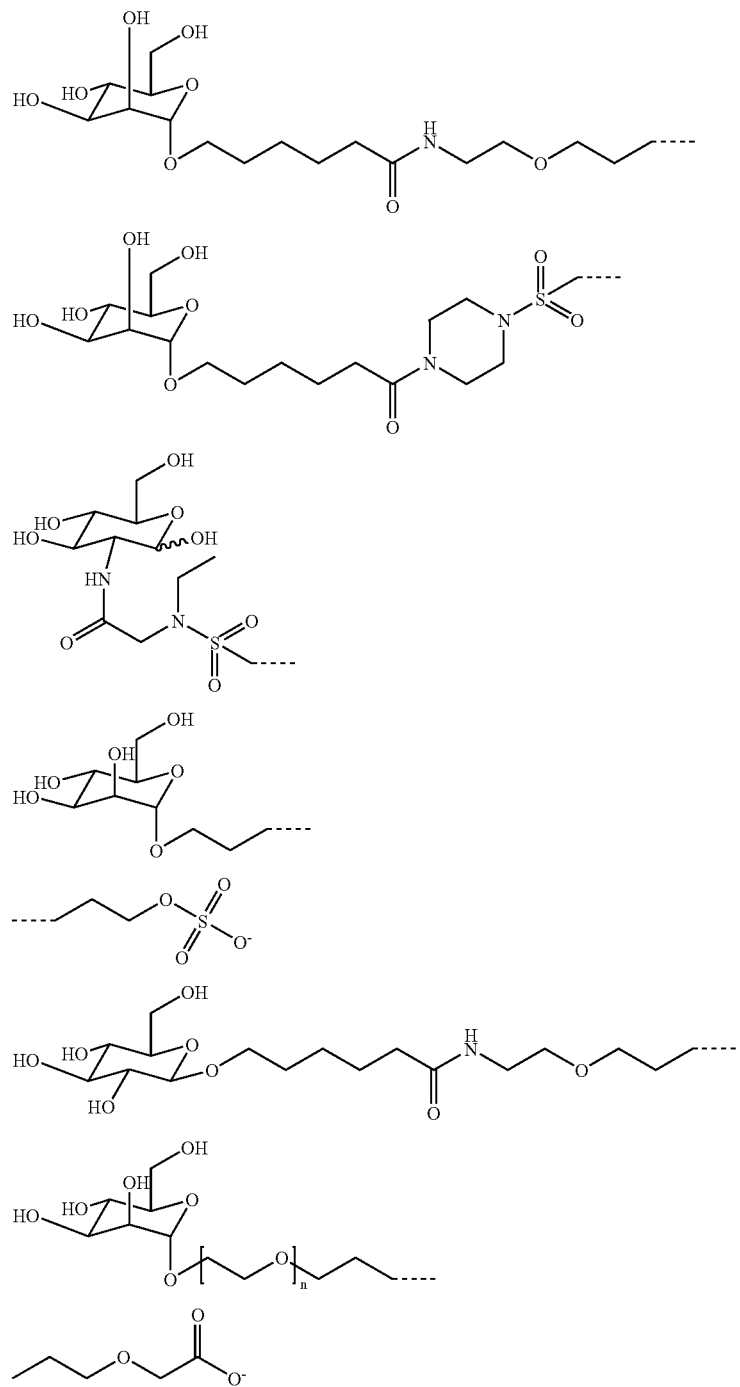

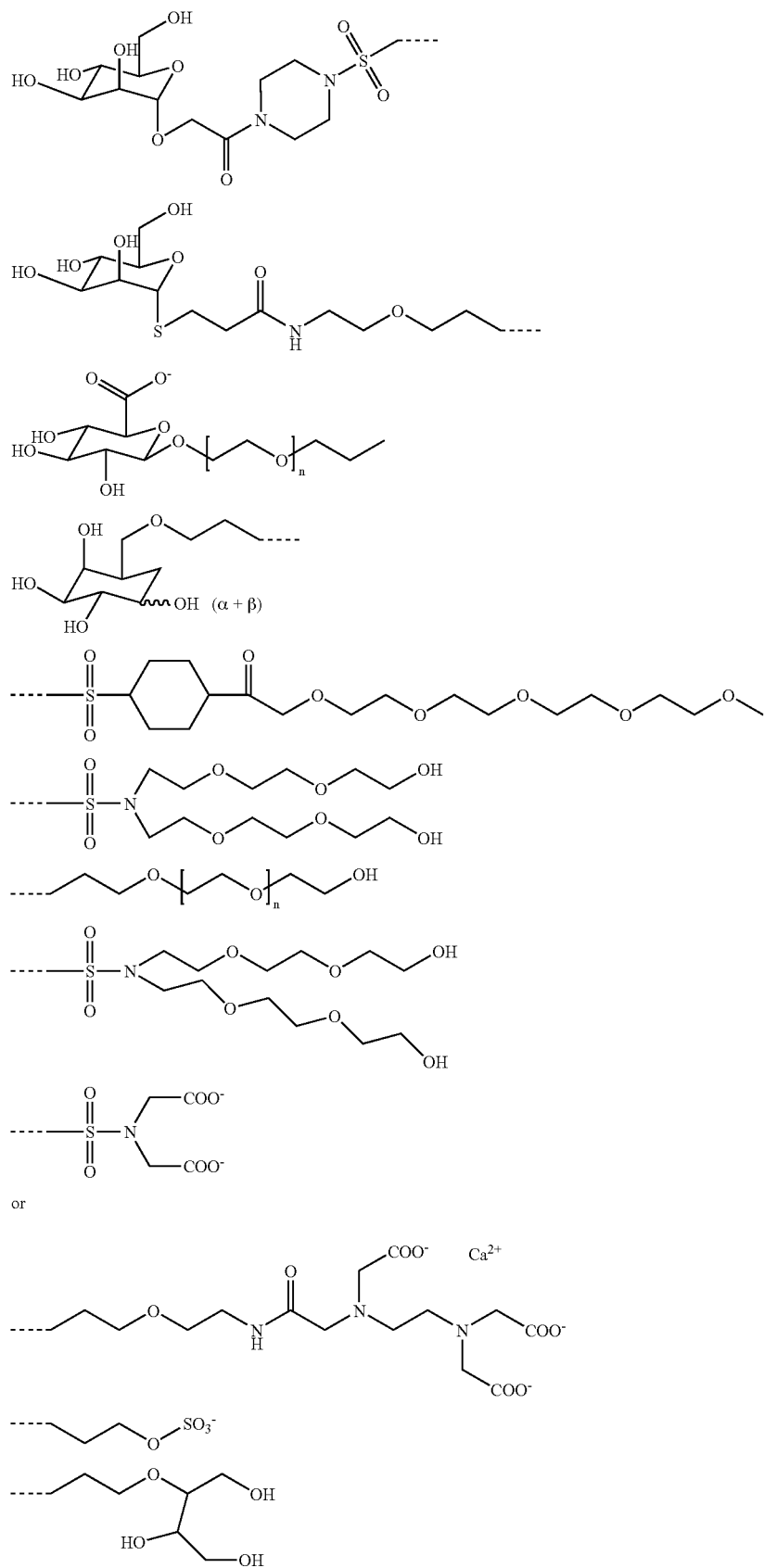

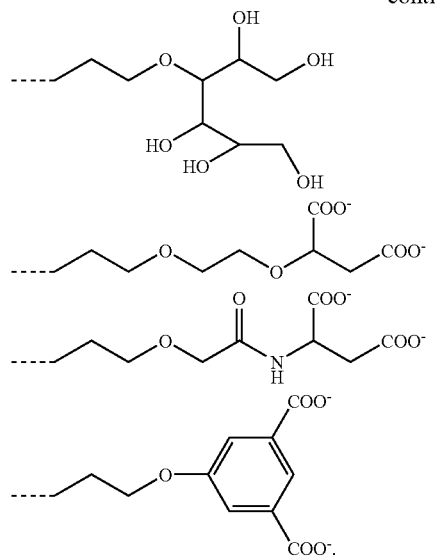

UNITED STATES PATENT AND TRADEMARK OFFICE
CERTIFICATE OF CORRECTION

PATENT NO. : 7,344,704 B2
APPLICATION NO. : 10/616511
DATED : March 18, 2008
INVENTOR(S) : Yoko Kawata It is certified that error appears in the above-identified patent and that said Letters Patent is hereby corrected as shown below:

Column 36, lines 6-7 reads "pertluoroalkyl" should read --perfluoroalkyl--
Column 36, line 44 reads "–NR-$_a$" should read -- –NR-$^a$--
Column 48, line 2 reads "–N(B$_1$)-" should read --N(B$^1$)- --
Column 51, line 52 reads "complex" should read --complex or--
Column 52, line 8 reads "IIe," should read --IIc,--
Column 52, line 42 reads "1to 3" should read --1 to 3--
Column 55, last line should read --and--
Column 57, line 64 reads "1to 3" should read --1 to 3--
Column 57, line 65 reads "1to 3" should read --1 to 3--
Column 61, line 50 reads ")C H" should read --) CH--
Column 62, line 57 reads "whereby" should read --wherein--
Column 62, line 60 reads "substances, conjugates" should read --substances, are conjugates--
Column 62, line 61 reads "and compounds" should read --or compounds--
Column 63, line 1 reads "whereby" should read --wherein--
Column 63, line 5 reads "whereby" should read --wherein--

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO.        : 7,344,704 B2                                                Page 1 of 1
APPLICATION NO. : 10/616511
DATED             : March 18, 2008
INVENTOR(S)       : Misselwitz It is certified that error appears in the above-identified patent and that said Letters Patent is hereby corrected as shown below:

Col. 51, line 9, should read -- $NHCOCH_2$ --.

Signed and Sealed this

Third Day of March, 2009

JOHN DOLL
*Acting Director of the United States Patent and Trademark Office*